(12) United States Patent
Kleiner et al.

(10) Patent No.: US 9,717,403 B2
(45) Date of Patent: Aug. 1, 2017

(54) METHOD AND APPARATUS FOR PERFORMING RETRO PERITONEAL DISSECTION

(71) Applicant: Jeffrey B. Kleiner, Aurora, CO (US)

(72) Inventors: Jeffrey Kleiner, Aurora, CO (US); Jeffrey Adair, Highlands Ranch, CO (US); Kevin Wiggins, Denver, CO (US)

(73) Assignee: Jeffrey B. Kleiner, Aurora, CO (US)

( * ) Notice: Subject to any disclaimer, the term of this patent is extended or adjusted under 35 U.S.C. 154(b) by 367 days.

(21) Appl. No.: 14/519,880

(22) Filed: Oct. 21, 2014

(65) Prior Publication Data

US 2015/0094533 A1 Apr. 2, 2015

Related U.S. Application Data

(63) Continuation-in-part of application No. 13/091,024, filed on Apr. 20, 2011, now Pat. No. 8,864,654,
(Continued)

(51) Int. Cl.
*A61B 1/04* (2006.01)
*A61B 1/32* (2006.01)
(Continued)

(52) U.S. Cl.
CPC ............ *A61B 1/32* (2013.01); *A61B 1/00103* (2013.01); *A61B 1/00135* (2013.01);
(Continued)

(58) Field of Classification Search
CPC .......... A61B 1/32; A61B 1/053; A61B 1/313; A61B 1/07; A61B 1/00154; A61B 17/3421
See application file for complete search history.

(56) References Cited

U.S. PATENT DOCUMENTS 3,060,972 A  10/1962 Sheldon
3,697,011 A  10/1972 Christensen et al.
(Continued)

FOREIGN PATENT DOCUMENTS

WO  WO 2004/030527  4/2004
WO  WO 2005/037149  4/2005
WO  WO 2011/011372  1/2011

OTHER PUBLICATIONS

Official Action for European Patent Application No. 12773535.5, dated Nov. 11, 2015 4 pages.
(Continued)

*Primary Examiner* — Timothy J Neal
(74) *Attorney, Agent, or Firm* — Sheridan Ross P.C.

(57) ABSTRACT

The foregoing application describes a system and method of performing a minimally invasive surgical operation. More specifically, the invention involves the use of disposable cannula and slender dilators of variable lengths, which incorporate a source of illumination to carry light to a surgical site and video capabilities for capturing and displaying images from a CMOS or CCD camera device. According to one embodiment, fiber optics run semi-circumferentially or along walls of the cannula/dilator and terminate at about a centimeter from the distal end of the cannula/dilator, thereby preventing illumination from "bottoming out" at the floor of the incision. According to one alternate embodiment, the light fibers may be fashioned in an annulus around one or more camera chips to provide illumination and video of the surgical site. In still another embodiment, the light fibers may be replaced by light emitting diodes in a more remote light source or alternatively at the distal-tip of the CMOS or CCD camera device.

29 Claims, 22 Drawing Sheets

Related U.S. Application Data which is a continuation-in-part of application No. 14/507,367, filed on Oct. 6, 2014, now Pat. No. 9,427,264, which is a continuation of application No. 13/754,042, filed on Jan. 30, 2013, now Pat. No. 8,870,882, which is a continuation of application No. 12/632,720, filed on Dec. 7, 2009, now Pat. No. 8,366,748, application No. 14/519,880, filed on Oct. 21, 2014, which is a continuation-in-part of application No. 12/965,654, filed on Dec. 10, 2010, now abandoned.

(60) Provisional application No. 61/326,138, filed on Apr. 20, 2010, provisional application No. 61/186,683, filed on Jun. 12, 2009, provisional application No. 61/120,260, filed on Dec. 5, 2008, provisional application No. 61/262,075, filed on Dec. 10, 2009, provisional application No. 61/323,984, filed on Apr. 14, 2010.

(51) Int. Cl.
| | |
|---|---|
| *A61B 1/06* | (2006.01) |
| *A61B 17/02* | (2006.01) |
| *A61B 17/34* | (2006.01) |
| *A61B 5/00* | (2006.01) |
| *A61B 1/00* | (2006.01) |
| *A61B 1/07* | (2006.01) |
| *A61B 1/05* | (2006.01) |
| *A61B 17/00* | (2006.01) |
| *A61B 90/30* | (2016.01) |
| *A61B 90/00* | (2016.01) |

(52) U.S. Cl.
CPC ........ *A61B 1/00154* (2013.01); *A61B 1/0607* (2013.01); *A61B 5/4893* (2013.01); *A61B 17/0218* (2013.01); *A61B 17/3421* (2013.01); *A61B 1/05* (2013.01); *A61B 1/0684* (2013.01); *A61B 1/07* (2013.01); *A61B 90/361* (2016.02); *A61B 2017/00022* (2013.01); *A61B 2017/00991* (2013.01); *A61B 2017/0256* (2013.01); *A61B 2017/0262* (2013.01); *A61B 2090/306* (2016.02); *A61B 2090/309* (2016.02)

(56) References Cited

U.S. PATENT DOCUMENTS

| | | |
|---|---|---|
| 3,741,496 A | 6/1973 | Beller |
| 3,836,092 A | 9/1974 | Hull |
| 3,900,021 A | 8/1975 | Makepeace et al. |
| 4,039,156 A | 8/1977 | Abraham |
| 4,041,939 A | 8/1977 | Hall |
| 4,047,524 A | 9/1977 | Hall |
| 4,462,402 A | 7/1984 | Burgio et al. |
| 4,467,478 A | 8/1984 | Jurgutis |
| 4,501,269 A | 2/1985 | Bagby |
| 4,522,270 A | 6/1985 | Kishi |
| 4,570,623 A | 2/1986 | Ellison et al. |
| 4,592,346 A | 6/1986 | Jurgutis |
| 4,706,653 A | 11/1987 | Yamamoto |
| 4,753,224 A | 6/1988 | Tojo |
| 4,834,069 A | 5/1989 | Umeda |
| 5,037,422 A | 8/1991 | Hayhurst |
| 5,053,038 A | 10/1991 | Sheehan |
| 5,055,104 A | 10/1991 | Ray |
| 5,058,823 A | 10/1991 | Emura et al. |
| 5,178,129 A | 1/1993 | Chikama et al. |
| 5,271,381 A | 12/1993 | Ailinger et al. |
| 5,290,295 A | 3/1994 | Querals et al. |
| 5,312,407 A | 5/1994 | Carter |
| 5,312,417 A | 5/1994 | Wilk |
| 5,324,307 A | 6/1994 | Jarrett et al. |
| 5,329,834 A | 7/1994 | Wong |
| 5,329,935 A | 7/1994 | Takahashi |
| 5,333,812 A | 8/1994 | Sato |
| 5,354,292 A | 10/1994 | Braeuer et al. |
| 5,395,372 A | 3/1995 | Holt et al. |
| 5,431,658 A | 7/1995 | Moskovich |
| D364,462 S | 11/1995 | Michelson |
| 5,483,951 A | 1/1996 | Frassica et al. |
| 5,512,036 A | 4/1996 | Tamburrino et al. |
| 5,527,312 A | 6/1996 | Ray |
| 5,531,664 A | 7/1996 | Adachi et al. |
| 5,541,191 A | 7/1996 | Skotnicki et al. |
| 5,549,607 A | 8/1996 | Olson et al. |
| 5,558,674 A | 9/1996 | Heggeness et al. |
| D374,283 S | 10/1996 | Michelson |
| 5,562,661 A | 10/1996 | Yoshimi et al. |
| 5,569,246 A | 10/1996 | Ojima et al. |
| 5,586,989 A | 12/1996 | Bray |
| 5,601,557 A | 2/1997 | Hayhurst |
| D378,409 S | 3/1997 | Michelson |
| 5,611,800 A | 3/1997 | Davis et al. |
| 5,634,925 A | 6/1997 | Urbanski |
| 5,653,763 A | 8/1997 | Errico et al. |
| 5,662,588 A | 9/1997 | Iida |
| 5,662,655 A | 9/1997 | Laboureau et al. |
| 5,665,122 A | 9/1997 | Kambin |
| 5,667,473 A | 9/1997 | Finn et al. |
| 5,688,285 A | 11/1997 | Yamada |
| 5,697,932 A | 12/1997 | Smith et al. |
| 5,704,892 A | 1/1998 | Adair |
| 5,741,253 A | 4/1998 | Michelson |
| 5,779,642 A | 7/1998 | Nightengale |
| 5,782,919 A | 7/1998 | Zdeblick et al. |
| 5,785,658 A | 7/1998 | Benaron et al. |
| 5,797,918 A | 8/1998 | McGuire et al. |
| 5,807,261 A | 9/1998 | Benaron et al. |
| 5,827,177 A | 10/1998 | Oneda et al. |
| 5,836,948 A | 11/1998 | Zucherman et al. |
| 5,836,958 A | 11/1998 | Ralph |
| 5,860,977 A | 1/1999 | Zucherman et al. |
| 5,865,746 A | 2/1999 | Murugesan et al. |
| 5,865,846 A | 2/1999 | Bryan et al. |
| 5,871,462 A | 2/1999 | Yoder et al. |
| 5,888,228 A | 3/1999 | Knothe et al. |
| 5,904,689 A | 5/1999 | Jonjic |
| 5,925,051 A | 7/1999 | Mikhail |
| 5,929,901 A | 7/1999 | Adair et al. |
| 5,944,658 A | 8/1999 | Koros et al. |
| 5,944,686 A | 8/1999 | Patterson et al. |
| 5,947,972 A | 9/1999 | Gage et al. |
| 5,961,445 A | 10/1999 | Chikama |
| 5,976,146 A | 11/1999 | Ogawa et al. |
| 5,986,693 A | 11/1999 | Adair et al. |
| 5,989,257 A | 11/1999 | Tidwell et al. |
| 5,997,895 A | 12/1999 | Narotam et al. |
| 6,004,326 A | 12/1999 | Castro et al. |
| 6,013,028 A | 1/2000 | Jho et al. |
| 6,019,765 A | 2/2000 | Thornhill et al. |
| 6,030,356 A | 2/2000 | Carlson et al. |
| 6,030,388 A | 2/2000 | Yoshimi et al. |
| 6,030,390 A | 2/2000 | Mehdizadeh |
| 6,030,401 A | 2/2000 | Marino |
| 6,033,408 A | 3/2000 | Gage et al. |
| 6,043,839 A | 3/2000 | Adair et al. |
| 6,045,555 A | 4/2000 | Smith et al. |
| 6,090,143 A | 7/2000 | Meriwether et al. |
| 6,096,080 A | 8/2000 | Nicholson et al. |
| 6,113,602 A | 9/2000 | Sand |
| 6,120,503 A | 9/2000 | Michelson |
| 6,136,001 A | 10/2000 | Michelson |
| 6,142,932 A | 11/2000 | Morizumi |
| 6,142,998 A | 11/2000 | Smith et al. |
| 6,146,420 A | 11/2000 | McKay |
| 6,149,096 A | 11/2000 | Hartley |
| 6,159,245 A | 12/2000 | Meriwether et al. |
| 6,180,085 B1 | 1/2001 | Achilefu |
| 6,184,923 B1 | 2/2001 | Miyazaki |
| 6,209,886 B1 | 4/2001 | Estes et al. |

(56) References Cited

U.S. PATENT DOCUMENTS

| | | | |
|---|---|---|---|
| 6,211,904 B1 | 4/2001 | Adair et al. |
| 6,216,573 B1 | 4/2001 | Moutafis et al. |
| 6,224,599 B1 | 5/2001 | Baynham et al. |
| 6,235,805 B1 | 5/2001 | Chang et al. |
| 6,238,397 B1 | 5/2001 | Zucherman et al. |
| 6,241,733 B1 | 6/2001 | Nicholson et al. |
| 6,241,769 B1 | 6/2001 | Nicholson et al. |
| 6,245,108 B1 | 6/2001 | Biscup |
| 6,258,094 B1 | 7/2001 | Nicholson et al. |
| 6,261,293 B1 | 7/2001 | Nicholson et al. |
| 6,261,295 B1 | 7/2001 | Nicholson et al. |
| 6,261,296 B1 | 7/2001 | Aebi et al. |
| 6,275,255 B1 | 8/2001 | Adair et al. |
| 6,287,319 B1* | 9/2001 | Aboul-Hosn ..... A61M 25/0125 606/192 |
| 6,290,724 B1 | 9/2001 | Marino |
| 6,299,613 B1 | 10/2001 | Ogilvie et al. |
| 6,309,395 B1 | 10/2001 | Smith et al. |
| 6,310,642 B1 | 10/2001 | Adair et al. |
| 6,325,805 B1 | 12/2001 | Ogilvie et al. |
| 6,328,738 B1 | 12/2001 | Suddaby |
| 6,336,928 B1 | 1/2002 | Guerin et al. |
| 6,364,828 B1 | 4/2002 | Yeung et al. |
| 6,364,880 B1 | 4/2002 | Michelson |
| 6,375,635 B1 | 4/2002 | Moutafis et al. |
| 6,451,017 B1 | 9/2002 | Moutafis et al. |
| 6,454,806 B1 | 9/2002 | Cohen et al. |
| 6,467,556 B2 | 10/2002 | Alsruhe |
| 6,500,206 B1 | 12/2002 | Bryan |
| 6,511,493 B1 | 1/2003 | Moutafis et al. |
| 6,520,976 B1 | 2/2003 | Gage |
| 6,524,318 B1 | 2/2003 | Longhini et al. |
| 6,543,392 B1 | 4/2003 | Ashton, III et al. |
| 6,564,078 B1 | 5/2003 | Marino et al. |
| 6,616,669 B2 | 9/2003 | Ogilvie et al. |
| 6,620,356 B1 | 9/2003 | Wong et al. |
| 6,641,613 B2 | 11/2003 | Sennett |
| 6,648,915 B2 | 11/2003 | Sazy |
| 6,652,533 B2 | 11/2003 | O'Neil |
| 6,669,710 B2 | 12/2003 | Moutafis et al. |
| 6,673,113 B2 | 1/2004 | Ralph et al. |
| 6,676,637 B1 | 1/2004 | Bonnette et al. |
| 6,679,887 B2 | 1/2004 | Nicholson et al. |
| 6,682,493 B2 | 1/2004 | Mirigian |
| 6,699,288 B2 | 3/2004 | Moret |
| 6,709,438 B2 | 3/2004 | Dixon et al. |
| 6,719,752 B2 | 4/2004 | Ouchi |
| 6,719,760 B2 | 4/2004 | Dorchak et al. |
| 6,719,795 B1 | 4/2004 | Cornwall et al. |
| 6,730,125 B1 | 5/2004 | Lin |
| 6,743,257 B2 | 6/2004 | Castro |
| 6,773,437 B2 | 8/2004 | Ogilvie et al. |
| 6,800,093 B2 | 10/2004 | Nicholson et al. |
| 6,824,565 B2 | 11/2004 | Muhanna et al. |
| 6,830,574 B2 | 12/2004 | Heckele et al. |
| 6,899,712 B2 | 5/2005 | Moutafis et al. |
| 6,923,792 B2 | 8/2005 | Staid et al. |
| 6,929,646 B2 | 8/2005 | Gambale |
| 6,942,665 B2 | 9/2005 | Gambale |
| 6,960,182 B2 | 11/2005 | Moutafis et al. |
| 6,962,592 B2 | 11/2005 | Gatturna et al. |
| 6,969,523 B1 | 11/2005 | Mattern et al. |
| 6,974,480 B2 | 12/2005 | Messerli et al. |
| 7,004,946 B2 | 2/2006 | Parker et al. |
| 7,008,431 B2 | 3/2006 | Simonson |
| 7,014,640 B2 | 3/2006 | Kemppainen et al. |
| 7,025,742 B2 | 4/2006 | Rubenstein et al. |
| 7,025,769 B1 | 4/2006 | Ferree |
| 7,030,904 B2 | 4/2006 | Adair et al. |
| 7,033,317 B2 | 4/2006 | Pruitt |
| 7,041,136 B2 | 5/2006 | Goble et al. |
| 7,077,864 B2 | 7/2006 | Byrd, III et al. |
| 7,094,257 B2 | 8/2006 | Mujwid et al. |
| 7,122,017 B2 | 10/2006 | Moutafis et al. |
| 7,135,043 B2 | 11/2006 | Nakahara et al. |
| 7,182,782 B2 | 2/2007 | Kirschman |
| 7,204,825 B2 | 4/2007 | Cimino et al. |
| 7,207,992 B2 | 4/2007 | Ritland |
| 7,214,186 B2 | 5/2007 | Ritland |
| 7,223,292 B2 | 5/2007 | Messerli et al. |
| 7,232,463 B2 | 6/2007 | Falahee |
| 7,238,203 B2 | 7/2007 | Bagga et al. |
| 7,255,703 B2 | 8/2007 | Mujwid et al. |
| 7,267,691 B2 | 9/2007 | Keller et al. |
| 7,288,093 B2 | 10/2007 | Michelson |
| 7,337,538 B2 | 3/2008 | Moutafis et al. |
| 7,341,590 B2 | 3/2008 | Ferree |
| 7,341,591 B2 | 3/2008 | Grinberg |
| 7,347,860 B2 | 3/2008 | Ouchi |
| 7,357,284 B2 | 4/2008 | Jauvin |
| 7,357,804 B2 | 4/2008 | Binder, Jr. et al. |
| 7,361,178 B2 | 4/2008 | Hearn et al. |
| 7,371,239 B2 | 5/2008 | Dec et al. |
| 7,373,197 B2 | 5/2008 | Daighighian et al. |
| 7,377,923 B2 | 5/2008 | Purcell et al. |
| 7,387,643 B2 | 6/2008 | Michelson |
| 7,399,041 B2 | 7/2008 | Prentner et al. |
| D574,495 S | 8/2008 | Petersen |
| 7,406,775 B2 | 8/2008 | Funk et al. |
| 7,410,334 B2 | 8/2008 | McGrew |
| 7,410,478 B2 | 8/2008 | Yang |
| 7,413,065 B2 | 8/2008 | Gauthier |
| 7,413,543 B2 | 8/2008 | Banik et al. |
| 7,421,772 B2 | 9/2008 | Gao et al. |
| 7,429,270 B2 | 9/2008 | Baumgartner et al. |
| 7,430,945 B2 | 10/2008 | Gauthier et al. |
| 7,431,711 B2 | 10/2008 | Moutafis et al. |
| 7,442,208 B2 | 10/2008 | Mathieu et al. |
| 7,455,157 B2 | 11/2008 | Kimes et al. |
| 7,473,255 B2 | 1/2009 | McGarity et al. |
| 7,476,226 B2 | 1/2009 | Weikel et al. |
| 7,478,577 B1 | 1/2009 | Wheeler |
| 7,481,766 B2 | 1/2009 | Lee et al. |
| 7,481,813 B1 | 1/2009 | Purcell |
| 7,485,145 B2 | 2/2009 | Purcell |
| D589,626 S | 3/2009 | Petersen |
| 7,501,073 B2 | 3/2009 | Wen et al. |
| 7,503,933 B2 | 3/2009 | Michelson |
| 7,503,934 B2 | 3/2009 | Eisermann et al. |
| 7,503,936 B2 | 3/2009 | Trieu |
| D590,943 S | 4/2009 | Petersen |
| D593,202 S | 5/2009 | Petersen |
| 7,531,003 B2 | 5/2009 | Reindel |
| 7,534,270 B2 | 5/2009 | Ball |
| 7,553,320 B2 | 6/2009 | Molz, IV et al. |
| 7,578,786 B2 | 8/2009 | Boulais et al. |
| 7,582,058 B1 | 9/2009 | Miles et al. |
| 7,582,107 B2 | 9/2009 | Trail et al. |
| 7,591,783 B2 | 9/2009 | Boulais et al. |
| D603,502 S | 11/2009 | Petersen |
| 7,618,423 B1 | 11/2009 | Valentine et al. |
| 7,621,955 B2 | 11/2009 | Goble et al. |
| 7,637,905 B2 | 12/2009 | Saadat et al. |
| 7,641,659 B2* | 1/2010 | Emstad ............. A61B 17/1735 600/210 |
| 7,655,027 B2 | 2/2010 | Michelson |
| 7,658,766 B2 | 2/2010 | Melkent et al. |
| 7,674,297 B2 | 3/2010 | Falahee |
| 7,677,418 B2 | 3/2010 | Henniges et al. |
| 7,686,805 B2 | 3/2010 | Michelson |
| 7,691,133 B2 | 4/2010 | Partin et al. |
| 7,693,562 B2 | 4/2010 | Marino et al. |
| 7,708,761 B2 | 5/2010 | Petersen |
| 7,717,685 B2 | 5/2010 | Moutafis et al. |
| 7,722,530 B2 | 5/2010 | Davison |
| 7,722,613 B2 | 5/2010 | Sutterlin et al. |
| 7,728,868 B2 | 6/2010 | Razzaque et al. |
| 7,730,563 B1 | 6/2010 | Sklar et al. |
| 7,734,327 B2 | 6/2010 | Colquhoun |
| 7,740,634 B2 | 6/2010 | Orbay et al. |
| 7,740,661 B2 | 6/2010 | Baratz et al. |
| 7,744,555 B2 | 6/2010 | DiMauro et al. |
| 7,744,637 B2 | 6/2010 | Johnson et al. |
| 7,744,973 B2 | 6/2010 | Schoenle et al. |

(56) References Cited

U.S. PATENT DOCUMENTS

| | | |
|---|---|---|
| 7,749,231 B2 | 7/2010 | Bonvallet et al. |
| 7,749,253 B2 | 7/2010 | Zucherman et al. |
| 7,749,269 B2 | 7/2010 | Peterman et al. |
| 7,749,273 B2 | 7/2010 | Cauthen et al. |
| 7,749,274 B2 | 7/2010 | Razian |
| 7,749,276 B2 | 7/2010 | Fitz |
| 7,749,279 B2 | 7/2010 | Twomey et al. |
| 7,751,865 B2 | 7/2010 | Jascob et al. |
| 7,753,911 B2 | 7/2010 | Ray et al. |
| 7,753,914 B2 | 7/2010 | Ruhling et al. |
| 7,753,938 B2 | 7/2010 | Aschmann et al. |
| 7,753,940 B2 | 7/2010 | Veldman et al. |
| 7,753,962 B2 | 7/2010 | Melder |
| 7,758,501 B2 | 7/2010 | Frasier et al. |
| 7,758,616 B2 | 7/2010 | LeHuec et al. |
| 7,758,617 B2 | 7/2010 | Iott et al. |
| 7,758,644 B2 | 7/2010 | Trieu |
| 7,758,648 B2 | 7/2010 | Castleman et al. |
| 7,762,950 B2 | 7/2010 | Hirata |
| 7,763,025 B2 | 7/2010 | Assell et al. |
| 7,763,035 B2 | 7/2010 | Melkent et al. |
| 7,763,055 B2 | 7/2010 | Foley |
| 7,763,078 B2 | 7/2010 | Peterman et al. |
| 7,763,080 B2 | 7/2010 | Southworth |
| D621,509 S | 8/2010 | Lovell |
| D622,395 S | 8/2010 | Iott et al. |
| 7,766,914 B2 | 8/2010 | McCormack et al. |
| 7,766,918 B2 | 8/2010 | Allard et al. |
| 7,766,930 B2 | 8/2010 | DiPoto et al. |
| 7,766,940 B2 | 8/2010 | Kwak et al. |
| 7,766,967 B2 | 8/2010 | Francis |
| 7,766,969 B2 | 8/2010 | Justin et al. |
| 7,769,422 B2 | 8/2010 | DiSilvestro et al. |
| 7,771,143 B2 | 8/2010 | Bharadwaj et al. |
| 7,771,475 B2 | 8/2010 | Michelson |
| 7,771,476 B2 | 8/2010 | Justis et al. |
| 7,771,479 B2 | 8/2010 | Humphreys et al. |
| 7,776,040 B2 | 8/2010 | Markworth et al. |
| 7,776,046 B2 | 8/2010 | Boyd et al. |
| 7,776,047 B2 | 8/2010 | Fanger et al. |
| 7,776,049 B1 | 8/2010 | Curran et al. |
| 7,776,075 B2 | 8/2010 | Bruneau et al. |
| 7,776,090 B2 | 8/2010 | Winslow et al. |
| 7,776,091 B2 | 8/2010 | Mastrorio et al. |
| 7,776,094 B2 | 8/2010 | McKinley et al. |
| 7,776,095 B2 | 8/2010 | Peterman et al. |
| 7,776,594 B2 | 8/2010 | Bays et al. |
| 7,780,707 B2 | 8/2010 | Johnson et al. |
| 7,794,396 B2 | 9/2010 | Gattani et al. |
| 7,794,501 B2 | 9/2010 | Edie et al. |
| 7,799,034 B2 | 9/2010 | Johnson et al. |
| 7,799,036 B2 | 9/2010 | Davison et al. |
| 7,799,053 B2 | 9/2010 | Haid et al. |
| 7,799,054 B2 | 9/2010 | Kwak et al. |
| 7,799,055 B2 | 9/2010 | Lim |
| 7,799,056 B2 | 9/2010 | Sankaran |
| 7,799,076 B2 | 9/2010 | Sybert et al. |
| 7,799,078 B2 | 9/2010 | Embry et al. |
| 7,799,083 B2 | 9/2010 | Smith et al. |
| 7,806,901 B2 | 10/2010 | Stad et al. |
| 7,811,327 B2 | 10/2010 | Hansell et al. |
| 7,811,329 B2 | 10/2010 | Ankney et al. |
| 7,815,681 B2 | 10/2010 | Ferguson |
| 7,819,801 B2 | 10/2010 | Miles et al. |
| 7,824,328 B2 | 11/2010 | Gattani et al. |
| 7,824,332 B2 | 11/2010 | Fakhrai |
| 7,824,410 B2 | 11/2010 | Simonson |
| 7,828,724 B2 | 11/2010 | Hosoi et al. |
| 7,828,804 B2 | 11/2010 | Li et al. |
| 7,828,845 B2 | 11/2010 | Estes et al. |
| 7,828,849 B2 | 11/2010 | Lim |
| 7,837,713 B2 | 11/2010 | Petersen |
| 7,837,732 B2 | 11/2010 | Zucherman et al. |
| 7,850,598 B2 | 12/2010 | Kobayashi et al. |
| 7,850,735 B2 | 12/2010 | Eisermann et al. |
| 7,850,736 B2 | 12/2010 | Heinz et al. |
| 7,918,845 B2 | 4/2011 | Saadat et al. |
| 8,043,211 B2 | 10/2011 | Hirata |
| 8,088,163 B1 | 1/2012 | Kleiner |
| 8,118,732 B2 | 2/2012 | Banik et al. |
| 8,289,381 B2 | 10/2012 | Bayer et al. |
| 8,337,455 B2 | 12/2012 | Boulais |
| 8,425,408 B2 | 4/2013 | Boulais et al. |
| 8,475,366 B2 | 7/2013 | Boulais et al. |
| 8,864,654 B2 | 10/2014 | Kleiner et al. |
| 2002/0022764 A1 | 2/2002 | Smith et al. |
| 2002/0168319 A1 | 11/2002 | Filleret et al. |
| 2003/0055418 A1 | 3/2003 | Tasto et al. |
| 2003/0083748 A1 | 5/2003 | Lee et al. |
| 2003/0195405 A1 | 10/2003 | Marino et al. |
| 2003/0222325 A1 | 12/2003 | Jacobsen et al. |
| 2004/0024466 A1 | 2/2004 | Heerklotz |
| 2004/0087956 A1 | 5/2004 | Weikel et al. |
| 2004/0138529 A1 | 7/2004 | Wiltshire et al. |
| 2004/0143330 A1 | 7/2004 | Sazy |
| 2004/0153158 A1 | 8/2004 | Errico et al. |
| 2004/0176853 A1 | 9/2004 | Sennett et al. |
| 2004/0230211 A1 | 11/2004 | Moutafis et al. |
| 2004/0249367 A1 | 12/2004 | Saadat et al. |
| 2005/0004433 A1 | 1/2005 | Hirata |
| 2005/0014996 A1 | 1/2005 | Konomura et al. |
| 2005/0075538 A1 | 4/2005 | Banik et al. |
| 2005/0080411 A1 | 4/2005 | Ouchi |
| 2005/0119527 A1 | 6/2005 | Banik et al. |
| 2005/0124993 A1 | 6/2005 | Chappuis |
| 2005/0124994 A1 | 6/2005 | Berger et al. |
| 2005/0149035 A1 | 7/2005 | Pimenta et al. |
| 2005/0149192 A1 | 7/2005 | Zucherman et al. |
| 2005/0159765 A1 | 7/2005 | Moutafis et al. |
| 2005/0177027 A1 | 8/2005 | Hirata |
| 2005/0182291 A1 | 8/2005 | Hirata |
| 2005/0191046 A1 | 9/2005 | Dehmel et al. |
| 2005/0216002 A1 | 9/2005 | Simonson |
| 2005/0216018 A1 | 9/2005 | Sennett |
| 2005/0240077 A1 | 10/2005 | Rovegno |
| 2005/0250990 A1 | 11/2005 | Le et al. |
| 2005/0267443 A1 | 12/2005 | Staid et al. |
| 2005/0272977 A1 | 12/2005 | Saadat et al. |
| 2005/0283150 A1 | 12/2005 | Moutafis et al. |
| 2006/0004367 A1 | 1/2006 | Alamin et al. |
| 2006/0058584 A1 | 3/2006 | Hirata |
| 2006/0063973 A1 | 3/2006 | Makower et al. |
| 2006/0074307 A1 | 4/2006 | Igarashi et al. |
| 2006/0095116 A1 | 5/2006 | Bolduc et al. |
| 2006/0100304 A1 | 5/2006 | Vresilovic et al. |
| 2006/0111779 A1 | 5/2006 | Petersen |
| 2006/0111780 A1 | 5/2006 | Petersen |
| 2006/0155170 A1 | 7/2006 | Hanson et al. |
| 2006/0167461 A1 | 7/2006 | Hawkins et al. |
| 2006/0178560 A1 | 8/2006 | Saadat et al. |
| 2006/0183975 A1 | 8/2006 | Saadat et al. |
| 2006/0189845 A1 | 8/2006 | Maahs et al. |
| 2006/0190081 A1 | 8/2006 | Kraus |
| 2006/0191975 A1 | 8/2006 | Adams et al. |
| 2006/0229550 A1 | 10/2006 | Staid et al. |
| 2006/0247650 A1 | 11/2006 | Yerby et al. |
| 2006/0264808 A1 | 11/2006 | Staid et al. |
| 2006/0270900 A1 | 11/2006 | Chin et al. |
| 2007/0003598 A1 | 1/2007 | Trieu |
| 2007/0073110 A1 | 3/2007 | Larson et al. |
| 2007/0088326 A1 | 4/2007 | Kennedy, II |
| 2007/0147033 A1 | 6/2007 | Ogawa et al. |
| 2007/0173695 A1 | 7/2007 | Hirata |
| 2007/0191684 A1 | 8/2007 | Hirata |
| 2007/0208423 A1 | 9/2007 | Messerli et al. |
| 2007/0213596 A1 | 9/2007 | Hamada |
| 2007/0213717 A1 | 9/2007 | Trieu |
| 2007/0213718 A1 | 9/2007 | Trieu |
| 2007/0213822 A1 | 9/2007 | Trieu |
| 2007/0242869 A1 | 10/2007 | Luo et al. |
| 2007/0244366 A1 | 10/2007 | Murata |
| 2007/0250166 A1 | 10/2007 | McKay |
| 2007/0270639 A1 | 11/2007 | Long |
| 2007/0270951 A1 | 11/2007 | Davis et al. |

(56) References Cited

U.S. PATENT DOCUMENTS

| | | |
|---|---|---|
| 2007/0276406 A1 | 11/2007 | Mahoney et al. |
| 2007/0288007 A1 | 12/2007 | Burkus et al. |
| 2008/0003255 A1 | 1/2008 | Kerr et al. |
| 2008/0009929 A1 | 1/2008 | Harris et al. |
| 2008/0015413 A1 | 1/2008 | Barlow et al. |
| 2008/0033440 A1 | 2/2008 | Moskowitz et al. |
| 2008/0039693 A1 | 2/2008 | Karasawa |
| 2008/0058606 A1 | 3/2008 | Miles et al. |
| 2008/0065110 A1 | 3/2008 | Duval et al. |
| 2008/0147018 A1 | 6/2008 | Squilla et al. |
| 2008/0147191 A1 | 6/2008 | Lopez et al. |
| 2008/0154375 A1 | 6/2008 | Serhan et al. |
| 2008/0154377 A1 | 6/2008 | Voellmicke |
| 2008/0195058 A1 | 8/2008 | Moutafis et al. |
| 2008/0195128 A1 | 8/2008 | Orbay et al. |
| 2008/0255564 A1 | 10/2008 | Michelson |
| 2008/0269904 A1 | 10/2008 | Voorhies |
| 2009/0012358 A1 | 1/2009 | Ichihashi et al. |
| 2009/0036739 A1 | 2/2009 | Hadani |
| 2009/0043312 A1 | 2/2009 | Koulisis |
| 2009/0076440 A1 | 3/2009 | Moutafis et al. |
| 2009/0076556 A1 | 3/2009 | McGarity et al. |
| 2009/0098184 A1 | 4/2009 | Govil et al. |
| 2009/0112062 A1 | 4/2009 | Bakos |
| 2009/0124860 A1 | 5/2009 | Miles et al. |
| 2009/0125066 A1 | 5/2009 | Krau et al. |
| 2009/0171150 A1 | 7/2009 | Iede et al. |
| 2009/0187072 A1* | 7/2009 | Manohara ......... A61B 1/00039 600/109 |
| 2009/0192350 A1 | 7/2009 | Meja |
| 2009/0192403 A1 | 7/2009 | Gharib et al. |
| 2009/0198245 A1 | 8/2009 | Phan |
| 2009/0198337 A1 | 8/2009 | Phan |
| 2009/0198338 A1 | 8/2009 | Phan |
| 2009/0198339 A1 | 8/2009 | Kleiner et al. |
| 2009/0203965 A1 | 8/2009 | Fujiyama et al. |
| 2009/0203967 A1 | 8/2009 | Branch et al. |
| 2009/0204148 A1 | 8/2009 | Lenke |
| 2009/0204159 A1 | 8/2009 | Justis et al. |
| 2009/0204220 A1 | 8/2009 | Trieu |
| 2009/0222011 A1 | 9/2009 | Lehuec et al. |
| 2009/0242612 A1 | 10/2009 | Adams et al. |
| 2009/0253958 A1 | 10/2009 | Ito et al. |
| 2009/0259108 A1 | 10/2009 | Miles et al. |
| 2009/0275995 A1 | 11/2009 | Truckai et al. |
| 2009/0287262 A1 | 11/2009 | Bertagnoli |
| 2009/0297136 A1 | 12/2009 | Lin |
| 2009/0299411 A1 | 12/2009 | Laskowitz et al. |
| 2009/0299412 A1 | 12/2009 | Marino |
| 2009/0299477 A1 | 12/2009 | Clayton et al. |
| 2009/0306692 A1 | 12/2009 | Barrington et al. |
| 2010/0010367 A1 | 1/2010 | Foley et al. |
| 2010/0010524 A1 | 1/2010 | Barrington et al. |
| 2010/0016903 A1 | 1/2010 | Matityahu et al. |
| 2010/0016972 A1 | 1/2010 | Jansen et al. |
| 2010/0016973 A1 | 1/2010 | de Villiers et al. |
| 2010/0030065 A1 | 2/2010 | Farr et al. |
| 2010/0036226 A9 | 2/2010 | Marino et al. |
| 2010/0036442 A1 | 2/2010 | Lauryssen et al. |
| 2010/0042221 A1 | 2/2010 | Boyd |
| 2010/0048993 A1 | 2/2010 | Shidara |
| 2010/0057208 A1 | 3/2010 | Dryer |
| 2010/0063516 A1 | 3/2010 | Parmer et al. |
| 2010/0063554 A1 | 3/2010 | Branch et al. |
| 2010/0076335 A1 | 3/2010 | Gharib et al. |
| 2010/0076445 A1 | 3/2010 | Pagano |
| 2010/0076446 A1 | 3/2010 | Gorek |
| 2010/0082036 A1 | 4/2010 | Reiley et al. |
| 2010/0087875 A1 | 4/2010 | McGahan et al. |
| 2010/0100141 A1 | 4/2010 | de Villiers et al. |
| 2010/0105111 A1 | 4/2010 | Asano et al. |
| 2010/0105986 A1 | 4/2010 | Miles et al. |
| 2010/0105987 A1 | 4/2010 | Miles et al. |
| 2010/0121365 A1 | 5/2010 | O'Sullivan et al. |
| 2010/0121453 A1 | 5/2010 | Peterman |
| 2010/0125333 A1 | 5/2010 | Zdeblick et al. |
| 2010/0125338 A1 | 5/2010 | Fitz |
| 2010/0131020 A1 | 5/2010 | Heinz et al. |
| 2010/0137690 A1 | 6/2010 | Miles et al. |
| 2010/0137923 A1 | 6/2010 | Greenhalgh et al. |
| 2010/0145390 A1 | 6/2010 | McCarthy et al. |
| 2010/0145391 A1 | 6/2010 | Kleiner |
| 2010/0145452 A1 | 6/2010 | Blaylock et al. |
| 2010/0145461 A1 | 6/2010 | Landry et al. |
| 2010/0160923 A1 | 6/2010 | Sand et al. |
| 2010/0160982 A1 | 6/2010 | Justis et al. |
| 2010/0161062 A1 | 6/2010 | Foley et al. |
| 2010/0161074 A1 | 6/2010 | McKay |
| 2010/0168755 A1 | 7/2010 | Reiley et al. |
| 2010/0168862 A1 | 7/2010 | Edie et al. |
| 2010/0174326 A1 | 7/2010 | Selover et al. |
| 2010/0191334 A1 | 7/2010 | Keller |
| 2010/0191337 A1 | 7/2010 | Zamani et al. |
| 2010/0199483 A1 | 8/2010 | Justis et al. |
| 2010/0204798 A1 | 8/2010 | Gerbec et al. |
| 2010/0217398 A1 | 8/2010 | Keller |
| 2010/0222784 A1 | 9/2010 | Schwab et al. |
| 2010/0222824 A1 | 9/2010 | Simonson |
| 2010/0228294 A1 | 9/2010 | LeHuec et al. |
| 2010/0228351 A1 | 9/2010 | Ankney et al. |
| 2010/0234848 A1 | 9/2010 | Sutterlin et al. |
| 2010/0234957 A1 | 9/2010 | Zdeblick et al. |
| 2010/0256767 A1 | 10/2010 | Melkent |
| 2010/0256768 A1 | 10/2010 | Lim et al. |
| 2010/0262241 A1 | 10/2010 | Eisermann et al. |
| 2010/0286778 A1 | 11/2010 | Eisermann et al. |
| 2010/0286784 A1 | 11/2010 | Curran et al. |
| 2010/0298938 A1 | 11/2010 | Humphreys et al. |
| 2010/0312103 A1 | 12/2010 | Gorek et al. |
| 2010/0312290 A1 | 12/2010 | McKinley et al. |
| 2010/0312347 A1 | 12/2010 | Arramon et al. |
| 2011/0034769 A1 | 2/2011 | Adair et al. |
| 2011/0071536 A1 | 3/2011 | Kleiner et al. |
| 2011/0108604 A1 | 5/2011 | Adams et al. |
| 2011/0156141 A1 | 6/2011 | Roig-Guitart et al. |
| 2011/0201887 A1* | 8/2011 | Greenblatt ......... A61B 17/3421 600/130 |
| 2011/0238006 A1 | 9/2011 | Crank |

OTHER PUBLICATIONS

Ray, C., "Facet Joint Disorders and Back Pain," published on Spine-Health, Dec. 10, 2002, available at www.spine-health.com/conditions/arthritis/facet-joint-disorders-and-back-pain, 1 page.

Staehler, R., "Spine Surgery for a Cervical Herniated Disc," published on Spine-Health, Jun. 12, 2002, available at www.spine-health.com/conditions/herniated-disc/spine-surgery-a-cervical-herniated-disc, 2 pages.

Staehler, R., "Summary of Cervical Herniated Disc Treatment Options," published on Spine-Health, Jun. 12, 2002, available at www.spine-health.com/conditions/herniated-disc/summary-cervical-herniated-disc-treatment-options, 1 page.

Ullrich, P.F., "Anterior Cervical Spinal Fusion Surgery," published on Spine-Health, Oct. 7, 2005, available at www.spine-health.com/treatment/back-surgery/anterior-cervical-spinal-fusion-surgery, 2 pages.

Ullrich, P.F., "Cervical Spinal Instrumentation," published on Spine-Health, Oct. 7, 2005, available at www.spine-health.com/treatment/back-surgery/cervical-spinal-instrumentation, 2 pages.

Wascher, T.M., "Anterior cervical decompression and spine fusion procedure," published on Spine-Health, Aug. 29, 2001, available at www.spine-health.com/treatment/spinal-fusion/anterior-cervical-decompression-and-spine-fusion-procedure, 2 pages.

"BAK® /Proximity™ (BP®)) Cage", Zimmer Website, as early as Oct. 23, 2007, available at http://www.zimmer.com/z/ctl/op/global/action/1/id/7930/template/MP/prcat/M6/prod/y, printed on Jun. 8, 2009, 1 page.

"BAK® Vista® Radiolucent Interbody Fusion System", Zimmer Website, as early as Oct. 25, 2005, available at http://www.zimmerindia.com/z/ctl/op/global/action/1/id/7809/template/MP/prcat/M6/prod/y, printed on Jun. 8, 2009, pp. 1-2.

(56) References Cited

OTHER PUBLICATIONS

"Facet Joint Syndrome," The Cleveland Clinic Foundation, copyright 1995-2008, printed Nov. 19, 2008, available at http://my.clevelandclinic.org/disorders/facet_joint_syndrome/hic_facet_joint_syndrome.aspx, 2 pages.

"Screws, Cages or Both", Spine Universe Website, as early as Aug. 18, 2002, available at http://www.spineuniverse.com/displayarticle.php/article1363.html, printed on Jun. 8, 2009, pp. 1-13.

"University of Maryland Spine Program: A Patient's Guide to Anterior Lumbar Interbody Fusion with Intervertebral Cages", University of Maryland Medical Center website, as early as 2003, available at http://www.umm.edu/spinecenter/education/anterior_lumbar_interbody_fusion_with_intervertebral_cages.htm, printed on Jun. 8, 2009, pp. 1-4.

"Vertebral column," from Wikipedia, the free encyclopedia, printed May 19, 2009, retrieved from http://en.wikipedia.org/wiki/Vertebral_column, 6 pages.

"Zygapophysial joint," from Wikipedia, the free encyclopedia, printed May 19, 2009, retrieved from http://en.wikipedia.org/wiki/Zygapophysial_joint, 2 pages.

International Search Report and Written Opinion for International (PCT) Patent Application No. PCT/US2012/021159, mailed May 23, 2012 11 pages.

International Preliminary Report on Patentability for International (PCT) Patent Application No. PCT/US2012/021159, mailed Oct. 31, 2013 9 pages.

Extended Search Report for European Patent Application No. 12773535.5, dated Aug. 20, 2014 7 pages.

Official Action for U.S. Appl. No. 13/091,024, mailed Apr. 26, 2013, 20 pages.

Final Action for U.S. Appl. No. 13/091,024, mailed Sep. 12, 2013, 18 pages.

Official Action for U.S. Appl. No. 13/091,024, mailed Jan. 9, 2014, 20 pages.

Notice of Allowance for U.S. Appl. No. 13/091,024, mailed Jun. 4, 2014 9 pages.

* cited by examiner

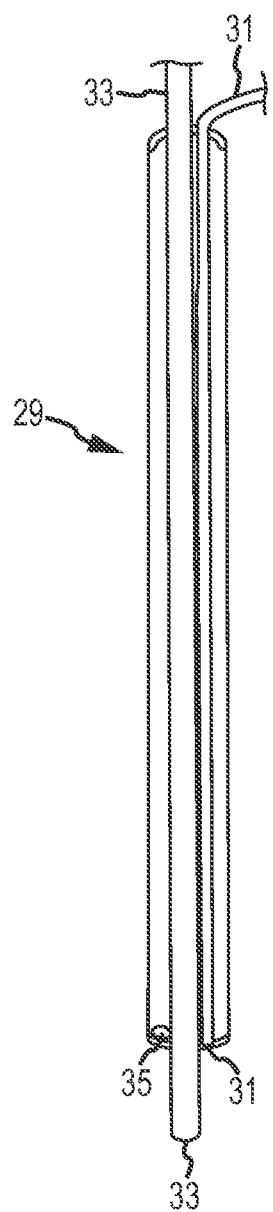
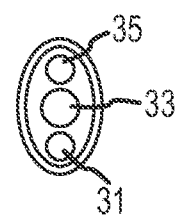
FIG.5
FIG.6

METHOD AND APPARATUS FOR PERFORMING RETRO PERITONEAL DISSECTION

CROSS-REFERENCE TO RELATED APPLICATIONS

The present application is a continuation-in-part of U.S. patent application Ser. No. 13/091,024 filed Apr. 20, 2011 (now U.S. Pat. No. 8,864,654, issued Oct. 21, 2014), entitled "Method and Apparatus for Performing Retro Peritoneal Dissection" and claims the benefits of and priority, under 35 U.S.C. §119(e), to U.S. Provisional Application Ser. No. 61/326,138, filed Apr. 20, 2010, entitled "Method and Apparatus for Performing Retro Peritoneal Dissection."

The present application is also a continuation-in-part of U.S. patent application Ser. No. 14/507,367, filed on Oct. 6, 2014, entitled "Apparatus and Method of Spinal Implant and Fusion," which is a continuation of Ser. No. 13/754,042, filed on Jan. 30, 2013 (now U.S. Pat. No. 8,870,882, issued Oct. 28, 2014), which is a continuation of Ser. No. 12/632,720, filed on Dec. 7, 2009 (now U.S. Pat. No. 8,366,748, issued on Feb. 5, 2013), and which claims priority from provisional patent application No. 61/186,683, filed Jun. 12, 2009; as well as provisional patent application No. 61/120,260, filed Dec. 5, 2008.

The present application is also a continuation-in-part of U.S. patent application Ser. No. 12/965,654, filed on Dec. 10, 2010, entitled "Lateral Based Retractor System", which is a non-provisional patent application which claims the benefit of priority from commonly owned U.S. Provisional Application Nos. 61/262,075, filed Dec. 10, 2009, and 61/323,984, filed Apr. 14, 2010. The entire contents of all of the above-referenced patent applications are hereby expressly incorporated by reference in this disclosure as if set forth fully herein.

FIELD OF THE INVENTION

This disclosure relates to human surgical procedures performed percutaneously, and more specifically to a novel retractor, neuro-monitoring probe and progressive cannula system that enhances illumination and visibility. The disclosure also relates to a system and method for providing one or more disposable or reusable camera/video devices, including camera/video devices incorporating CCD and/or CMOS technology.

BACKGROUND OF THE INVENTION

Surgical procedures to address illness, disease or injury vary depending on a number of factors, including the ability of the surgeon(s) to access and perform the necessary procedures at the affected site. As one example, individuals who suffer degenerative disc disease, natural spine deformations, a herniated disc, spine injuries or other spine disorders often require surgery on the affected region to relieve pain or prevent further injury to the spine and nerves. Spinal surgery may involve removal of damaged joint tissue, insertion of a tissue implant and/or fixation of two or more adjacent vertebral bodies. These procedures are often difficult due to the location of the spine and adjacent nerves, sensitive anatomy, etc. The surgical procedure will vary in approach and duration depending on the nature and extent of the injury.

One particular type of spinal surgery is referred to as "fusion." Fusion of vertebral bodies involves fixation of two or more adjacent vertebrae. This procedure may be performed through introduction of rods or plates, and screws or other devices into a vertebral joint to join various portions of a vertebra to a corresponding portion on an adjacent vertebra. Fusion may occur in the lumbar, interbody or cervical spine region of a patient. A fusion is designed to stop and/or eliminate all motion in the spinal segment by destruction of some or all of the joints in that segment and further utilizing bone graft material and/or rigid implantable fixation devices for securing the adjacent vertebrae. By eliminating movement, back pain and further degenerative disc disease may be reduced or avoided. Fusion requires tools for accessing the vertebrae, such as surgical cannulae for "minimally-invasive" surgical procedures, and other tools for implanting the desired implant, bioactive material, etc. Such procedures often require introduction of additional tools to prepare a site for implantation. These tools may include drills, drill guides, debridement tools, irrigation devices, vises, clamps, cannula, and other insertion/retraction tools.

Spinal surgeries may be performed by a number of different "minimally-invasive" procedures, as opposed to conventional surgical procedures and methods, which typically require cutting of muscles, removal of bone, and retraction of other natural elements. With minimally invasive spinal surgery, a less destructive approach to the spine is carried out by using portals, which take advantage of anatomy and current technology to limit the damage to intervening structures.

Typically, skeletal landmarks are established fluoroscopically and a small incision is made over the landmark(s). According to methods known in the prior art, a series of dilators are applied until one or more cannula is placed over the anatomic structure. A microscope is then placed over the operative site. The microscope provides illumination and magnification with a three dimensional view of the anatomical site. While this process provides substantial advantages relative to open surgery, it requires the use of an operating microscope. This particular piece of equipment is extremely expensive (most quality brands are in the $250,000 range). The microscope is an unwieldy device requiring uncomfortable gyrations of the surgeon's back and neck in order to gain the necessary view and is a nuisance to drape (a large, sterile plastic bag has to be placed over the eight foot tall structure). The illumination is also difficult to direct due to the size of the microscope.

A significant danger of performing intervertebral operations or accessing an intervertebral space during spine surgery is that of inadvertently contacting or damaging the para-spinal nerves, including the exiting nerve roots, traversing nerves and the nerves of the cauda equina. The exact location of these para-spinal nerves cannot be determined prior to the commencement of surgery, and therefore are dependent on a surgeon's ability to visually locate the same after the initial incision is made. Moreover, intervertebral spaces in the spine have other sensitive nerves disposed at locations which are not entirely predictable prior to insertion of the surgical tool into the intervertebral area. Accordingly, the danger of pinching or damaging spinal nerves when accessing an intervertebral space has proven to be quite limiting to the methods and devices used during minimally invasive spinal surgery. In addition, as cannula are received through the patient's back, such as when performing minimally invasive spinal surgery, minor blood vessels are ruptured, thereby blocking the surgeon's vision inside the intervertebral region after the cannula has been inserted. Other anatomical features at a particular patient may also destruct the surgeon's view or make it difficult to provide illumination within the cannula.

Lateral based spinal surgery is a known alternative to conventional surgical procedures, and is generally referred to as a "minimally-invasive" procedure. Lateral based procedures offer the advantages of shorter recovery times, reduced blood loss, reduced post-operative complications, and shorter operating times than conventional procedures and methods. For example, one surgical approach for spinal fusion using a minimally invasive technique is known as "lumbar interbody fusion" or LIF for short. Other known examples of lateral based approaches include the Nuvasive XLIF procedure and Medtronic D-LIF System. However, these systems and methods have problems and shortcomings, including, but not limited to, limited visualization and lighting in the surgical area, increased risk of impinging upon the nerves of the lumbosacral plexus, and the ilioinguinal and genitofemoral nerves and the risk of devices and/or instruments becoming dislodged during the various procedures, among others. These problems, alone or in combination, may result in post-operative pain and discomfort experienced by patients of lateral based spinal surgery. In some instances, these problems require or otherwise lead to additional surgeries, further complicating the likelihood of recovery and successful fusion.

Various devices and surgical access systems are known in the art to facilitate minimally invasive surgical procedures while allowing for a sufficiently large surgical area. These devices may include a series of tools which, when consecutively inserted, serve to gradually expand an area, including cannula. Retractors are useful for gradually dilating the area of an incision or surgical opening in order to form a desired amount of space within which various procedures may be conducted. Retractors may take the form of a single device that may be inserted into a work area and expanded at the direction of a user, thus allowing for the creation and maintaining of a surgical work space. Many retractors fail to provide independent illumination sources or allow the surgeon to visualize the path of access to the surgical site. As these retractors are often the first (or one of the first) tools used in the procedure, providing adequate illumination and enhancing visualization are important to the success of the operation. Thus, there is a present felt need for an improved retractor with enhanced illumination that otherwise improves the visibility for the surgeon, and for a method of retrofitting an existing retractor with apparatus to accomplish this objective.

Other problems experienced in minimally invasive surgical procedures include the risk of injury caused during the initial probing and dissecting of tissue between the incision and the surgical site. Typically, such probing is done using a finger or a slender dilator or other tool, which is used to navigate through the soft tissue, anatomy, and ultimately reach the desired point of access to the surgical site. During this probing, there is increased risk to injury to the lumbar plexus, particularly when the surgeon is attempting to access the lumbar spine. In addition, there is also an increased risk to the patient's anatomy, and to undesired dissection of various anatomical features between the incision and the surgical site. This risk of injury typically increases as the probe is inserted deeper into the body of a patient, and continues after the probe has been fully inserted and continuing through dilation, such as by inserting one or more progressive surgical cannula around the dilator proceeds. Damage to the peritoneal membrane, colon perforation, ureteral or great vessel injury can be the result of the "blind" dissection and is major reason why the lateral, transpoas approach is not a more commonly performed surgical procedure. Thus, there is a deep felt need in the art to mitigate these potentially catastrophic complications, and to address the other problems associated with performing these procedures in a "blind" manner.

Typically, as these processes for accessing the surgical site are done blind (i.e., without vision of where the probe is directed), it is not uncommon that the probing instrument(s) intersect and/or dissect the patient's anatomy, intercept nerves, sensitive tissue, rupture arteries, etc. Thus, there is also a need for an improved tool for initially dilating and accessing the tissue between the incision and the surgical site. There is a further need for an improved system and method for providing a surgeon with visibility of this area, to assist with the navigation through the tissue, anatomy, etc. and to provide enhanced illumination for a minimally invasive surgical procedure.

The disclosure of the invention herein addresses these and other problems by providing a system and method for achieving an endoscopic approach to a surgical site, coupled with the use of a unique illumination and video capability. The system of the invention is preferably achieved by incorporating a camera chip in the apparatus of the system, thereby obviating the need and disadvantages of the operating microscope and other expensive and cumbersome instrumentation. These and other considerations are addressed by the present disclosure in more detail in the Summary and Detailed Description.

SUMMARY OF THE INVENTION

Incorporated by reference in their entireties are the following U.S. patents and patent applications directed generally to methods and apparatus related to spinal procedures, thus providing written description support for various aspects of the present disclosure. The U.S. patents and pending applications incorporated by reference are as follows: U.S. Pat. Nos. 7,406,775 to Funk, et al.; 7,387,643 to Michelson; 7,341,590 to Ferree; 7,288,093 to Michelson; 7,207,992 to Ritland; 7,077,864 Byrd III, et al.; 7,025,769 to Ferree; 6,719,795 to Cornwall, et al.; 6,364,880 to Michelson; 6,328,738 to Suddaby; 6,290,724 to Marino; 6,113,602 to Sand; 6,030,401 to Marino; 5,865,846 to Bryan, et al.; 5,569,246 to Ojima, et al.; 5,527,312 to Ray; and 2008/0255564 to Michelson. These references assist in explaining the current state of the art for surgical instruments generally, and provide additional written support for the various apparatus and methods described herein.

According to one particular embodiment of the present disclosure, the invention involves the use of a disposable cannula of variable lengths, which are applied over the dilator tools. These cannulas can have a variety of shapes depending upon the surgical requirement. Ovoid, egg-shaped or round cannulas are contemplated and may further comprise an angled working edge as described in greater detail herein. The devices described herein are unique in that they have incorporated a source of illumination, preferably attached to the walls of the cannula, which emit light to the base of the portal and enhance illumination within the cannula.

According to yet another aspect of the present disclosure, a modified retractor according to various embodiments is described that incorporates illumination and/or video capabilities. The modified retractor cooperates with cannula described in greater detail below to permit a surgeon to avoid nerves, aberrant vessels and other anatomical features such as the kidney, ureter, peritoneal membrane, etc.

According to one embodiment, the retractor includes an extension or "periscope" feature that moves longitudinally along the shaft of the blade of the retractor to exclude retroperitoneal fat or other tissue that otherwise obscures the view of the surgeon along the outer surface of the blade of the retractor, where one or more cannula may be mounted.

According to one embodiment of the disclosure, the illumination is provided by way of fiber optic strands or bundles. The fiber optics can run circumferentially or along one or more walls of the cannula, and preferably terminate at least a centimeter from the bottom of the device. This prevents the illumination from "bottoming out" at the floor of the incision. Additionally, the light fibers may be fashioned in an annulus around a camera chip device to provide illumination to the surgical site where images are being captured by the camera chip device. In still another embodiment, the light fibers may be replaced by one or more LEDs in a remote light source or at the distal-tip of the camera chip device. The light source may come from an external device such as a headlight lamp, or a standard-type light source commonly found in operating rooms which plugs into an adaptor on the disposable cannula.

According to embodiments described herein, the system comprises a disposable cannula that has at least one slot through which the camera chip device(s) can be passed and inserted on a composite insert, which preferably fits in a tongue and groove fashion down the slot of the cannula. The camera chip device may have associated wide-angle optics and its composite insert can be easily removed/adjusted during the course of the operation for cleaning or when the cannula needs to be re-directed or reoriented during the course of the surgery.

The camera chip device, which according to a preferred embodiment is based on either CCD or CMOS technology, may have the necessary video-processing circuitry onboard the camera chip device housing, or the video-processing circuitry may be housed separately, several meters away from the camera chip device, and connected by a cable or alternatively via wireless transmission. For further details on the type of camera chip device according to a preferred embodiment of the present disclosure, applicant hereby incorporates by reference in its entirety the disclosure of U.S. Pat. No. 6,310,642.

According to one embodiment, an apparatus and method and provided whereby, instead of the surgeon viewing the operative site through the oculars of the microscope, the anatomy is presented on a screen in front of him (or her) and in front of the assistant(s). Due to the camera chip device and associated optics housing being placed directly at the operative site, the image collected is free from the distortions and the "field-flattening" effects found when using complex optical stacks commonly found in operating microscopes and endoscopes. This results in a significant increase in "depth-cues" and color-reproduction and in turn improves visibility. The camera technology provides a three dimensional-type picture to the surgeon with enhanced illumination, and without the extra costs of adding a second camera device and expensive intra-ocular optical orientations. The costs of the microscope and its maintenance, plastic draping, sterility/contamination issues and surgeon fatigue are either eliminated or at least substantially reduced.

According to yet another embodiment of the present disclosure, a tool is provided that comprises at least one CMOS or CCD video imaging device, which permits a user to view images captured by the CMOS or CCD imaging device of the disc space or other surgical area to be operated on. For example, one or more angled tools may incorporate a video insert (described in greater detail below), for capturing and viewing images of the intervertebral disc space during or after dissection has occurred. This may be accomplished by providing a CMOS or CCD camera device at the distal end of the one or more angled tools, and either wirelessly or hardwire transmitting the images captured by that CMOS or CCD camera to a display. As one other example, one or more scraping or debridement tools may incorporate the video insert described in greater detail below, for capturing and viewing images of the intervertebral disc space after and during dissection. This capacity allows for a more complete and safe disc space preparation. A more precise carpentry of the disc space allows for an increased potential for fusion and a reduction of vertebral endplate or soft tissue injury. This may be accomplished by providing a CMOS or CCD camera at the distal end of the one or debridement tools, and either wirelessly or hardwire transmitting the images captured by that CMOS or CCD camera to a display.

One having skill in the art will appreciate that the apparatus described herein, according to various embodiments of the present disclosure, may have various sizes. The sizes of the various elements of embodiments of the present disclosure may be sized based on factors including, for example, the anatomy of the patient, the person operating the apparatus, the surgical site location, physical features of any implanted device required with the surgical procedure, including, for example, width, length and thickness, and the size of the drill or other surgical tool being used with the apparatus, and other factors.

According to one embodiment, the illumination and camera/video capabilities described herein may be provided with one or more cannula having a shape other than round (e.g., oval, pointed, square cornered, egg-shaped etc.) and having an end (e.g., the end inserted into the patient, distal from the user) that is angled and/or tapered and/or shaped to be ideally seated in a particular surgical site. Asymmetrical cannulas may allow visualization of the facet joint of the spine, for example. An "egg-shaped" cross section may allow for the best view of the facet joint and further minimizes the medial-lateral dissection that a round cannula would require. Such shapes are specifically contemplated for incorporating the illumination and camera/video apparatus described herein.

Still other aspects of the invention are directed to cannula instruments that have a patient contacting end that is adjustable to assume a predetermined conformation. Thus, in one embodiment, material forms the end that comes into contact with bone, tissue, and especially as it nears nerve tissue, with such cannula end material being malleable to an extent necessary for the surgeon to mold the end such that it achieves the desired contours or avoids particular structures encountered in any particular surgery. By way of example but not limitation, if a bony outcropping, a nerve fiber, etc. is perceived by the surgeon, the cannula tip end can be adjusted to avoid undesired contact or interference with such tissues or structures.

In particular embodiments, the ability to adjust the geometric parameters of the cannula end may be achieved by manipulation of the other end of the instrument. For example, providing a turnable component at the opposite end of the instrument, the shape of the other end of the instrument (i.e. the end inserted into the patient) can be adjusted to either expand circumference, reduce circumference, render the opening more or less oblong, etc. In such a manner, it is possible to avoid having to remove the instrument or cannula from the patient's site to adjust the morphology of the instrument, thus saving time, avoiding undesired reinsertion procedures, etc.

According to another embodiment of the present disclosure, a system is provided wherein the cannula further include one or more electrical probes at the exit portal, which are adapted to assist the surgeon in identifying the presence and location of nerves as the probe is advanced during minimally-invasive surgery, thereby providing further assistance and feedback for guiding the path of the cannula and other surgical instruments to be inserted into the surgical site.

An expandable tip cannula or dilator may be provided, which functions both as an access portal for surgery and as a system for nerve surveillance, such that the presence and relative position of para-spinal nerves, for example, can be detected as the expandable tip cannula is inserted through the patient's facia and musculature. One particular advantage of determining the position of the lumbosacral plexus with respect to the distal tip of the cannula/dilator is that the lumbosacral plexus can be avoided or gently moved out of the surgeon's way while inserting the cannula/dilator.

According to one embodiment, the present disclosure provides a system of cannulas adapted to assist the surgeon in guiding the path of surgical instruments received into the intervertebral space, while identifying the presence and location of para-spinal nerves as the cannula is advanced to a patient's intervertebral space during minimally invasive surgery. In various aspects of the present disclosure, probes of the type described in greater detail herein may be comprised of one or more electrodes powered at a low level to sense the position of a para-spinal nerve through continuous real time electromyographic monitoring. Alternatively, these electrodes can be powered at a higher level such that they operate to cauterize blood vessels. Safety systems ensure that power levels sufficient to cause cauterization are not activated if a nerve is sensed to be near the electrodes at the distal end of the cannula.

According to yet another embodiment of the present disclosure, a system is provided where the cannula or dilator further include one or more electrical probes at the exit portal/patient contacting end, which are adapted to assist the surgeon in identifying the presence and location of nerves as the probe is advanced during minimally-invasive surgery, thereby providing a device for guiding the path of other surgical instruments to be inserted into the intervertebral space.

According to one embodiment, the present disclosure provides a system of cannulas adapted to assist the surgeon in guiding the path of surgical instruments received into an intervertebral space, while identifying the presence and location of para-spinal nerves as the cannula is advanced to a patient's intervertebral space during minimally invasive surgery. In various aspects of the present disclosure, the system of cannulas may further comprise of one or more electrodes powered at a low level to sense the position of the nerves of the lumbo-sacral plexus through continuous real time electromyographic monitoring. Alternatively, these electrodes can be powered at a higher level such that they operate to cauterize blood vessels. Safety systems ensure that power levels sufficient to cause cauterization are not activated if a nerve is sensed to be near the electrodes at the distal end of the cannula.

One having skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, rubber, latex, synthetic rubber, and other fiber-encased resinous materials, synthetic materials, polymers, and natural materials.

One having skill in the art will appreciate that embodiments of the present disclosure may be controlled by means other than manual manipulation. Embodiments of the present disclosure may be designed and shaped such that the apparatus may be controlled, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators.

The Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. Further details and description of embodiments of the present disclosure are provided in the Appendix A to this application.

BRIEF DESCRIPTION OF THE DRAWINGS

The present disclosure relates to systems and methods for accessing intervertebral space and facilitating the use of surgical tools and inserting spine implants between vertebral bodies. Those of skill in the art will recognize that the following description is merely illustrative of the principles of the disclosure, which may be applied in various ways to provide many different alternative embodiments. This description is made for illustrating the general principles of the teachings of this disclosure invention and is not meant to limit the inventive concepts disclosed herein.

The accompanying drawings, which are incorporated in and constitute a part of the specification, illustrate embodiments of the disclosure and together with the general description of the disclosure given above and the detailed description of the drawings given below, serve to explain the principles of the disclosures.

FIG. 5 is a side sectional view of a dilator that includes a neuro-monitoring lead that extends from the body of the dilator, illumination means, and at least one other lumen for a camera device according to one embodiment of the present disclosure;

FIG. 6 shows a cross-sectional view of the dilator of FIG. 5;

It should be understood that the above-referenced drawing figures are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Various embodiments of the apparatus and methods of the present disclosure are described in detail below. The following patents are hereby incorporated by reference for the express purpose of describing the technology related to the use of illumination and video capabilities described herein, including the use of camera chips and CCD or CMOS technology: U.S. Pat. Nos. 6,310,642; 6,275,255; 6,043,839; 5,929,901; 6,211,904; 5,986,693; and U.S. Pat. No. 7,030,904.

Referring now to FIGS. 1-4, a modified retractor according to embodiments of the present disclosure is shown, which incorporates illumination and/or video capabilities of the nature described herein. This "Sherrill" retractor comprises a longitudinal blade, which extends longitudinally a length sufficient for inserting into a patient to assist in retracting tissue between the incision and the surgical site, and may incorporate one more lumens internal to the blade for providing illumination means and/or CMOS or CCD video capabilities. This "Sherrill" retractor may alternatively be used, or used in connection with the dilator or wand described below in connection with FIGS. 5-6. Further details of this modified retractor are provided below.

Figure 1:
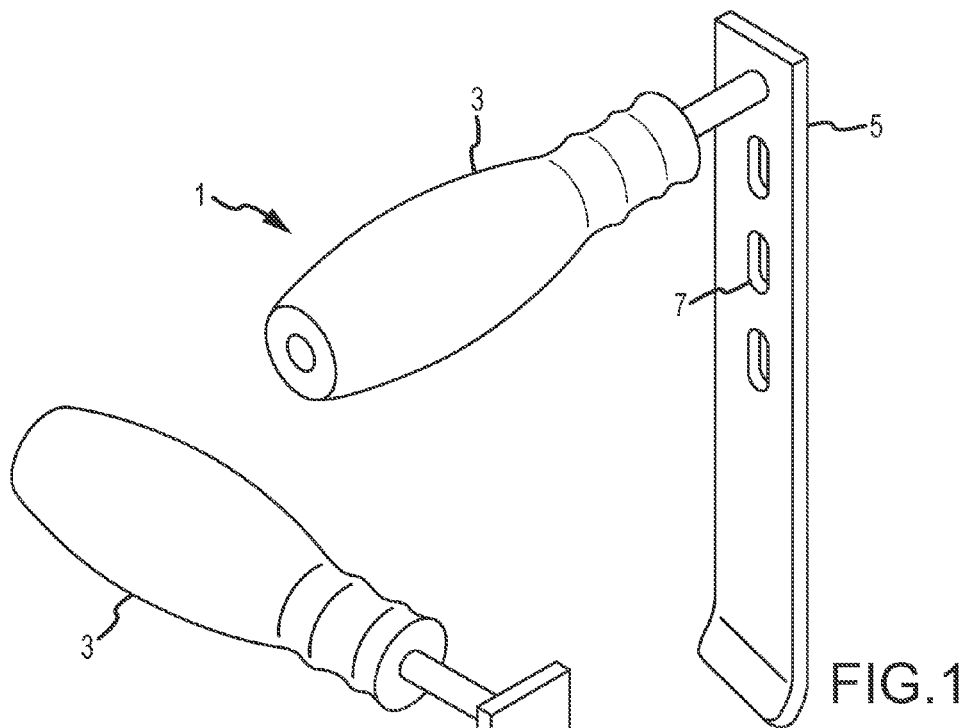
FIG. 1 is a perspective view of a modified retractor according to one embodiment of the present disclosure.
Figure 2:
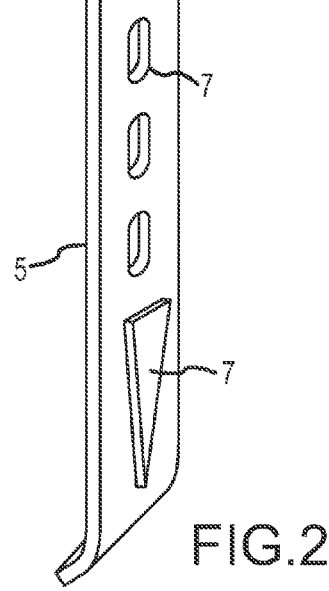
FIG. 2 is another perspective view of the modified retractor of FIG. 1.

FIG. 1 is a perspective view of the modified retractor 1 according to one embodiment of the present disclosure. The modified retractor 1 comprises a handle 3 and a generally planar blade 5 that has a length sufficient to reach a variety of surgical sites. The retractor 1 may further comprise one or more visual landmarks 7 along the length of the blade 5 as shown in FIGS. 1 and 2. According to one embodiment, the handle 3 may be detachable from the blade 5 and may also be substantially hollow for housing a power source, such as a battery, as described in further detail below in connection with FIG. 3.

FIG. 2 depicts another perspective view of the modified retractor 1 of FIG. 1. In a preferred embodiment, the blade 5 of the modified refractor (such as the one shown in FIG. 4) comprises two thin edges formed along at least a portion of the sides of the blade 5, which are convenient for use in attaching a semi-circular or semi-oval shaped cannula (shown in FIG. 4 as 25) by sliding the cannula over the two thin edges of the blade 5. Thus, according to one embodiment shown in FIG. 4, a cannula 25 is provided with two corresponding grooves or lips 27 along the surface of the cannula body, and oriented to couple with the two thin edges of the modified retractor.

In this manner, a surgeon using the modified refractor may first insert the retractor, retract any tissue and other anatomical features between the incision and the surgical site, and then attach the cannula 25 by sliding the cannula 25 along the two thin edges in a longitudinal direction relative to the blade 15 of the retractor. In another embodiment, the two thin edges may have slightly raised surfaces or bosses for facilitating this attachment via a tongue and groove connection. In one embodiment, the handle 13 of the modified retractor extends in generally the same direction as the blade 15 of the modified retractor, or is offset from the plane of the blade by an angle less than 90 degrees to facilitate this interconnectivity between the modified retractor and the cannula described above.

Figure 3:
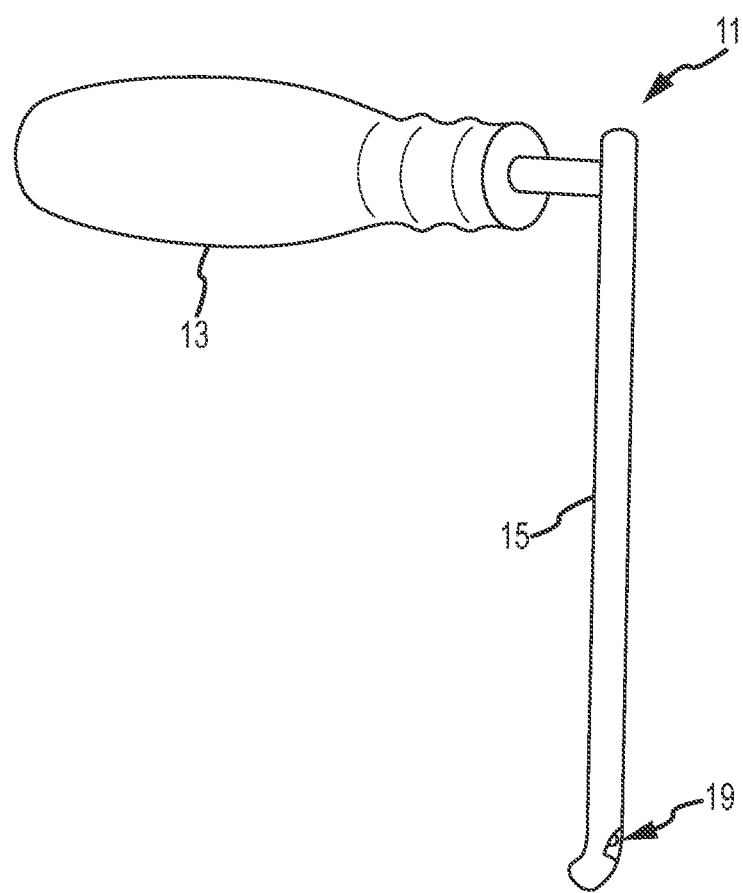
FIG. 3 is a conceptual diagram of the modified retractor of FIG. 1 with a means for providing illumination at or near the distal end of the modified retractor.
Figure 4:
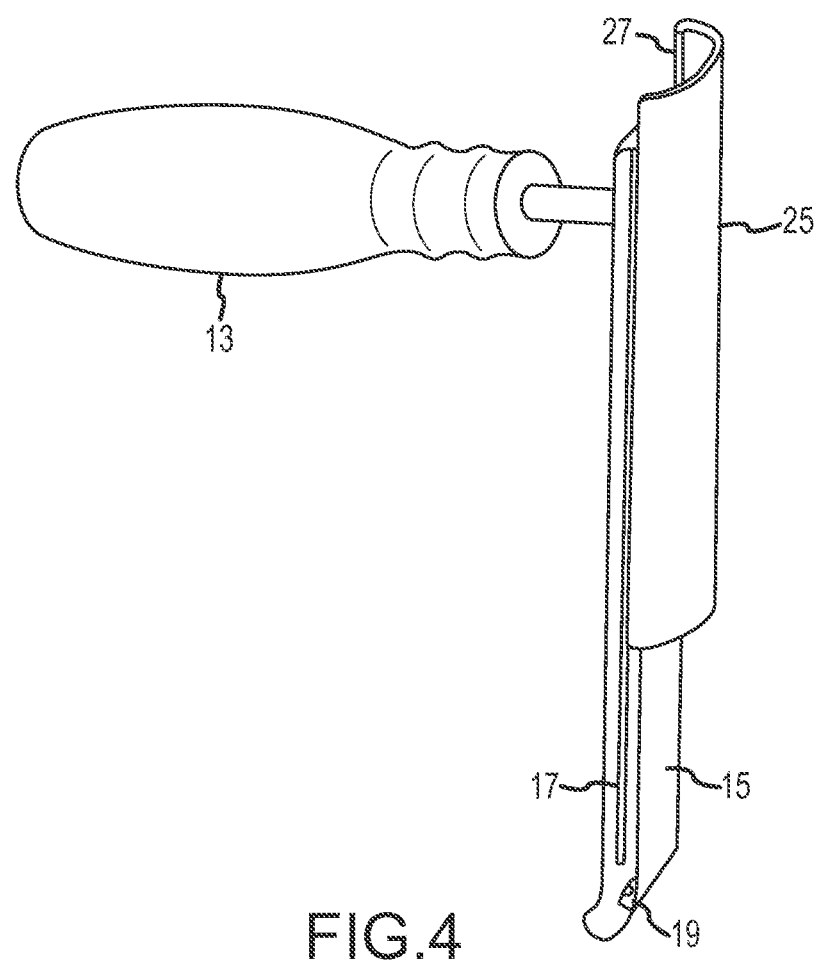
FIG. 4 is a conceptual diagram of the modified retractor of FIG. 1 mating with a semi-circular cannula and having enhanced illumination for improving visibility within the cannula.

According to one embodiment of the present disclosure, a method is disclosed whereby the dissecting finger is followed by this modified "Sherrill" retractor, which preferably incorporates one or more light emitting diodes 19 at its distal end as shown in FIG. 3, and a handle 13 containing the LED power source. According to this method, as the surgeon advances his blunt finger dissection of the retroperitoneal space, the Sherrill retractor 11 follows the finger with a visible path preventing inadvertent damage to intra- and retroperitoneal structures. The Sherrill retractor 11 is preferably modified to incorporate one or more camera devices (such as CMOS camera chips) at its contacting end and secured within a housing for allowing safe, visual placement through the dissected retroperitoneal space. This technique and associated apparatus shown in FIGS. 1-4 may be particularly useful for a surgeon attempting placement of the retractor onto the psoas muscle while avoiding the ilioinguinal and genitofemoral nerves on the surface of the muscle.

According to one embodiment, a flexible sleeve may be fabricated to fit over the body of an existing retractor or distractor device and incorporate the lumens or channels for inserting one or more fiber optic strands or bundles, and may also include a slot for inserting a camera insert such as the type described above. Therefore, existing retractors and distracters manufactured by various parties such as Medtronic and Nuvasive may incorporate the concepts of the present disclosure despite having no prefabricated lumens or slots for accommodating the necessary illumination and/or video capabilities discussed herein.

FIGS. 5-6 show a specific dilator or "wand" according to one preferred embodiment, which may be used for achieving the objectives described herein. In this embodiment, the dilator or wand 29 has a generally ovoid cross-sectional shape and is sufficient in size to accommodate a plurality of lumens, through which a CMOS or CCD camera insert 31 and/or illumination means 35 such as one or more light emitting diodes may be incorporated. According to a preferred embodiment, the dilator or wand 29 comprises at least one lumen 33 which extends beyond the length of the generally ovoid section of the dilator or wand, which may be used in a tapering configuration (and according to one alternative embodiment, a telescoping configuration) for gently probing through tissue, achieving vision (via CMOS or CCD video technology) of the anatomy through which the surgeon must navigate prior to securing the cannula to the surgical site, etc. In this embodiment, the dilator or wand 29 also comprises a lumen 33 through which one or more conductive materials may be inserted for stimulation of the various nerves of the psoas. This dilator 29 may also house illumination means 35, such as fiber optic strands and/or LED devices, for allowing a light source at the useable end of the dilator or wand 29.

In use, this enhanced dilator 29 allows the surgeon to have direct visualization and illumination of the retroperitoneal space, and allows simultaneous stimulation of the psoas or other spinal nerves, via one or more electrical probes which are incorporated into one of the plurality of lumens of the dilator 29. This dilator 29 therefore serves as a guide, which allows the surgeon to safely and securely reach the surgical site without causing damage to any of the patient's anatomy, and continue with application of progressively larger dilators and working cannula (including those described herein) without causing injury to the patient.

The dilator 29 may vary in length, according to the patient and the unique anatomy presented for the surgical operation. According to a preferred embodiment, the length dilator 29 is in the range of 50-500 millimeters in length, and the diameter is approximately 2-10 480 millimeters. The material of the dilator 29 is preferably selected from the group consisting of aluminum, iron, titanium, steel, stainless steel, surgical stainless steel of the general alloy type of iron, carbon, chromium (12-20%) molybdenum (0.2-3%) and nickel (8-12%), martensitic steel, grade 316L austenitic steel, grade 316LVM austenitic steel, grade 316 stainless steel, medical grade plastic and PEEK.

According to one embodiment of the present disclosure, the same distal end of the dilator 29 that comprises a CCD or CMOS video device 31 further comprises a conductive material, which is capable of transmitting signals, such as neurological signals to a measuring device for detecting one or more nerves in-between the incision and the surgical site. This distal neuro-monitoring tip may be made of a variety of different conductive materials, including but not limited to copper, brass, aluminum, metal alloy, inherently conductive polymers or any of the known polymers having a conductive filler, such as metal fillers, metal-cooled glass and/or carbon fiber fillers.

One or more CCD or CMOS camera devices 31 located at the distal end of the dilator 29 may be surrounded by a lens, and the lens made of a conductive glass, wherein the conductivity of the device and the lens of the device are accomplished in a single integrated apparatus. According to a preferred embodiment, the distal end of the dilator 29 is generally ovoid in shape and provides for a compound radii, which further assists in moving soft and often sensitive tissue away from the tip of the dilator as it is inserted into the patient. Similarly, the conductive material at the distal tip of the dilator 29 is preferably ovoid, and permits material to be moved gently away from the device at is progressed deeper into the incision.

According to various embodiments, the dilator 29 further comprises one or more fiber optic fibers which extend longitudinally down the shaft of the dilator for providing illumination. According to one embodiment, the one or more strands are positioned proximate to the CCD or CMOS video device 31, such that the CCD or CMOS video device 31 has adequate illumination for capturing images at the distal end of the dilator 29. This illumination also allows a surgeon to achieve adequate visualization, both with the naked eye and through images captured by the CCD or CMOS video device 31. In an alternate embodiment, the illumination is proved by one or more LED devices adjacent the CCD or CMOS video device 31.

Referring again to the drawing figures, according to one embodiment, the dilator 29 may be comprised of a generally cylindrical body, having a generally ovoid cross-section as shown in FIG. 6, and may incorporate multiple lumens extending therethrough. One or more internal lumens may incorporate the fiber optic illumination strands and/or the CCD or CMOS video device, while the second lumen may provide a channel for receiving signals via the conductive material at the distal end of the dilator. This second lumen may alternately serve as a guide for wire anchors to be positioned from the end opposite the CCD or CMOS video device, which allow the surgeon to insert, for example, 0.0625 inch K-wire or other suitable wire or fastening device to secure to the disc space.

Figure 19:
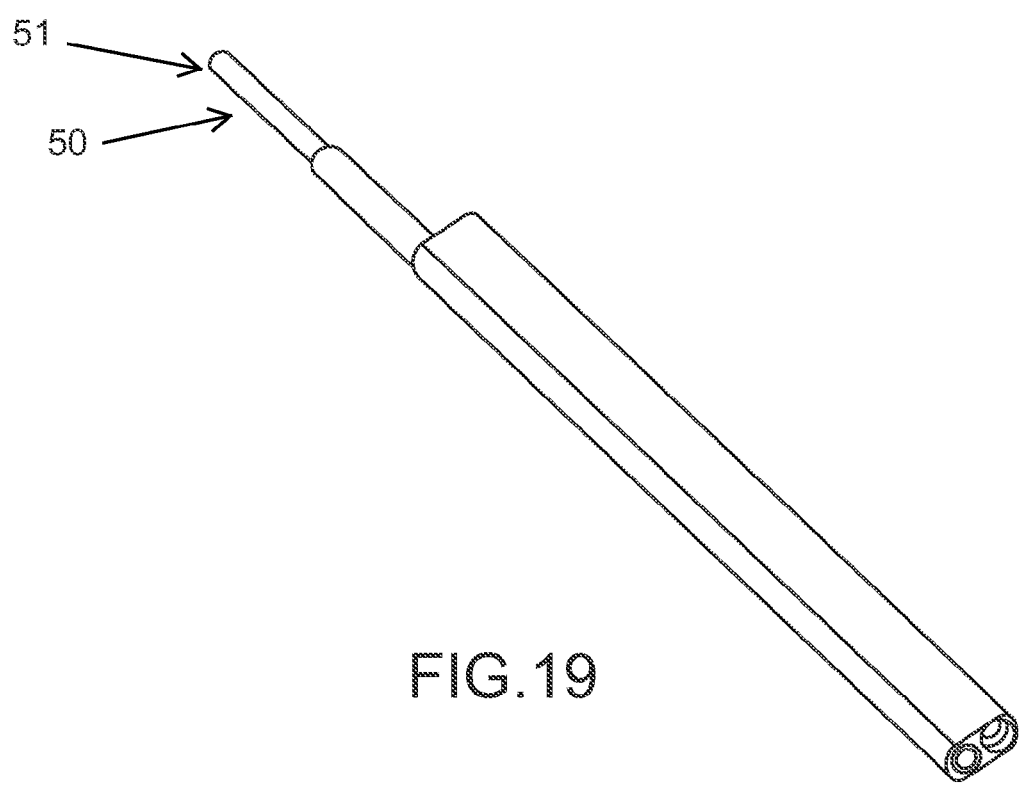
FIG. 19 is a perspective view of a dilator tool according to one alternative embodiment of the present disclosure.

According to the embodiment shown in the drawing FIGS. 5-6 and particularly in the alternate embodiment shown in FIG. 19, the illumination and CCD or CMOS camera device may extend a distance beyond the generally cylindrical body of the dilator, such that the illumination and video device precede the navigation of the generally cylindrical body of the dilator, thereby permitting the surgeon to see and illuminate tissue, sensitive anatomy, etc. prior to impact by the dilator.

In use, a method of retro peritoneal dissection involves using one or more slender video dilators to gently probe through the incision and to view the images captured by the CCD or CMOS video device located on or near the distal end of the one or more slender dilators. As the surgeon encounters sensitive anatomical features, such as the patient's intestine, images of those anatomical features will become apparent to the surgeon via the display. The images of other anatomical features are also captured by the CCD or CMOS video device during dissection and insertion of the one or more slender dilators.

If certain anatomical features cannot be moved from the path of the dilator, the approach of the surgeon may be adjusted accordingly, and the dilator inserted around these features to avoid undesired dissection. This in turn allows the surgeon to view the path to the disc space, achieve the desired approach and insure that any further instrumentation or apparatus that are inserted through the incision do not encounter the sensitive anatomical features of the patient, and further insure that the cannula are properly seated adjacent the disc space.

Once the slender dilator has been inserted through the sensitive anatomy of the patient and approaches the desired surgical cite, the surgeon can further use the images captured from the CCD or CMOS video device to find the desired location of the disc space where the operation will proceed, dissection of the disc space will occur, etc. According to one embodiment, this method involves incorporating one or more cannula, which may be inserted over the video dilator, and seated on the disc space using the same path achieved by insertion of the video dilator. Additional cannula may then be placed over this initial cannula, until the desired access has been achieved. Once the cannula are in position over the slender dilator, the surgeon may remove the dilator and use direct vision through the cannula, or use the slender dilator to continue to view the disc space, or both.

According to varying embodiments, this dilator and cannula system allows simultaneous illumination and video imaging of the path through which the surgeon must navigate to reach the surgical site. This in turn reduces the risk of unwanted dissection, unwanted exposure and damage to surrounding nerves, soft or sensitive tissue, etc. In use, the dilator may be further manipulated in conjunction with the Sherrill retractor (see FIG. 1), wherein this Sherrill retractor provides a narrow yet deep retracting blade, which may or may not incorporate a illuminated end, such as by an LED, which allows the surgeon to initially probe using the blade and remove the initial tissue immediately below the incision. The Sherrill retractor blade therefore provides an initial depth of illumination and navigation, and clears a passage for further insertion of the dilator. Multiple views of the Sherrill retractor used in combination with the dilator are shown in the appended drawing FIGS. 1-4.

This approach and apparatus is further advantageous in that it alleviates a common problem experienced by surgeons performing minimally invasive surgical procedures, which is fatigue. Using this dilator apparatus and method the surgeon is not required to position himself or herself over the cannula, or over a cumbersome or bulky microscope, which are frequently required in other surgical methods. By avoiding the positioning of the surgeon over the patient's body, the cannula, the microscope, etc., the surgeon is able to avoid significant discomfort and fatigue, which occurs naturally over time, particularly due to the surgery exceeding two hours to complete, or in some cases, 8 to 10 hours to complete. Using this method, the surgeon further avoids the necessary precautions required for exposure to radiographic imaging using this method. For example, the surgeon, by eliminating the use of x-rays and other radiographic equipment, is not required to wear a lead vest, a neck shield, a leaded glass face shield, etc. This further reduces the weight that the surgeon must bear during the operation, further reducing the stress and fatigue on the surgeon during the procedure.

Although not shown in the enclosed drawing figures, the slender dilator may further comprise one more mechanisms for cleaning or clearing the lens of the CMOS video camera at the distal end of the dilator. According to one embodiment, the clearing of the lens may occur mechanically, such as by a wiping mechanism, applied to a dilator such as the one shown in FIGS. 5-6 and 19. This wiping mechanism may be mechanically operated from the opposite distal end of the slender dilator as the one incorporating the CCD or CMOS video device, such as by a trigger mechanism. In operation, by moving the trigger longitudinally along the axis of the dilator, the surgeon can move the wiping device across the lens of the CCD or CMOS video device, thereby clearing the lens of loose tissue, mucus, or other fluids.

According to one particular embodiment of the present disclosure, the invention involves the use of one or more cannula of variable lengths, which according to a preferred embodiment are applied over one or more dilators. These cannulas can have a variety of shapes depending upon the surgical requirement. Ovoid, egg-shaped or round have been described, and an angled working edge is further contemplated. The apparatus of this system are unique in that they have incorporated a source of illumination built into the walls of the cannula, which carry the light to the base of the portal of the cannula, and further incorporate camera/video capabilities.

Attention is drawn to FIGS. 7-18. One or more cannula in a preferred embodiment are disclosed, and are generally tubular in form, with a support wall which has an open distal end and an open proximal end. The distal end may be rounded so that tissues are pushed aside gently as the cannula is inserted through the patient. A bore runs the length of the cannula from the open distal end to the open proximal end, and provides access to the targeted spinal area for instrument insertion, and insertion and removal of implant devices, arthroscopic devices, graft materials, bone cement, and other materials and devices.

A cross-sectional shape of the support wall of the bore may be round, oval, elliptical, crescent-shaped, a half-sphere or half-oval or another suitable shape. The cross-sectional shape has a width, which may have a measurement in the range of about 10-50 millimeters. Preferably the width is in the range of about 15-35 millimeters. The open proximal end may further comprise a plurality of grip features which allow the surgeon to grip the cannula. The cannula may be formed of substantially sterile material, and may further comprise biocompatible polymers, elastomers, ceramics, or aluminum or other metals. According to one embodiment, the cannula is disposable. In another embodiment, the cannula is reusable.

One aspect of the present disclosure is providing a cannula with an incorporated illumination source that provides enhanced illumination to the surgical site sufficient to incorporate camera/video capabilities with the apparatus and system. According to one particular embodiment, the illumination is provided by incorporating one or more fiber optic strands in the tubular body of the cannula. The fiber optics can run circumferentially or along opposite walls of the cannula and preferably terminate at least a centimeter from the bottom of the device. The light fibers may be fashioned in an annulus around a camera device (See FIG. 17) to provide illumination to the surgical site where images are being captured by the camera chip device. In still another embodiment, the light fibers may be replaced by one or more LEDs (See FIGS. 14-16) in a remote light source or at the distal-tip of the camera chip device. The light source may come from an external device such as a 620 headlight lamp, or a standard-type light source commonly found in operating rooms which plugs into an adaptor on the disposable cannula.

Figure 7:
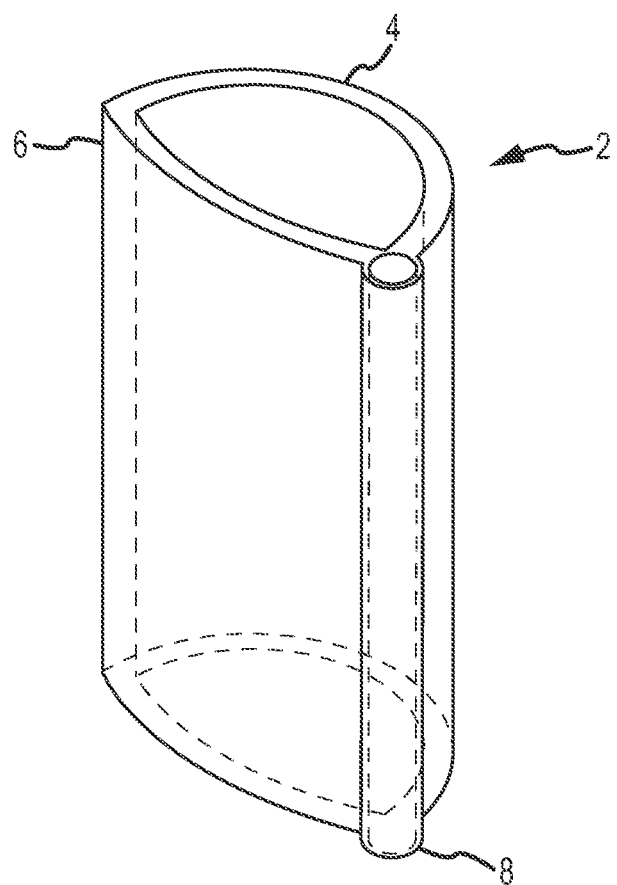
FIG. 7 is a perspective view of a cannula according to a preferred embodiment of the present disclosure.

Referring now in detail to FIGS. 7-13, various cannula according to one embodiment of the system of the present disclosure are shown. In FIG. 7, a perspective view of a cannula 2 is shown having a generally circular first surface 4 and a generally 625 elliptical second surface 6. About one intersection of the first surface 4 and second surface 6 is a channel or lumen 8 for inserting one or more fastening devices, such as a screw, for securing the cannula 2 to the surgical site. The cannula 2 shown in FIG. 7 may vary in lengths and widths according to the anatomy of the patient, the surgical site to be accessed, and other factors relating to the surgery, including the tools or implants that are required to 630 be inserted into the cannula 2.

Figure 8:
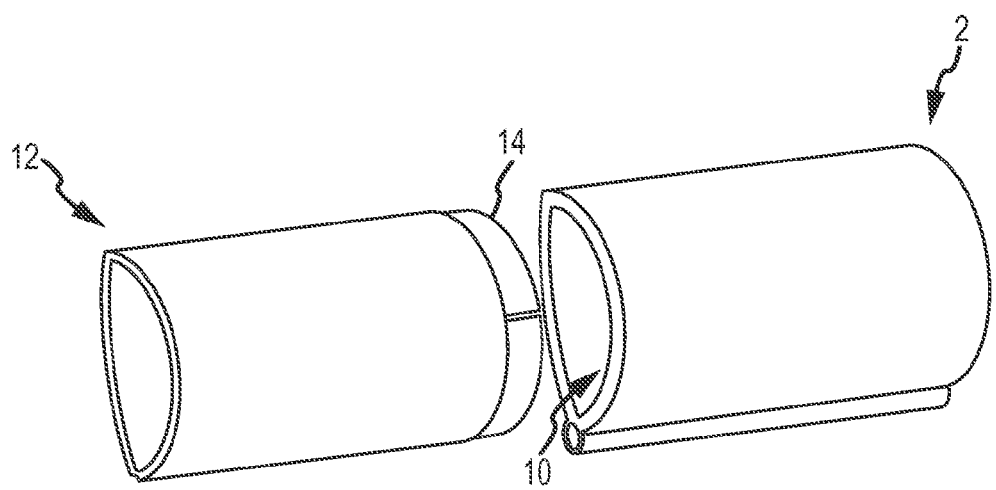
FIG. 8 is a perspective view of an interlocking cannula with the cannula of FIG. 7.

Referring now to FIG. 8, the cannula 2 shown in FIG. 7 may be coupled to one or more additional cannula 12, for example, by way of a compression fit between the two or more cannula 2, 12. As shown in FIG. 8, the second cannula 12 may be inserted by a compression relief 14 formed about one distal end of the second cannula 12 that is 635 dimensioned to fit in compression with the tubular body 10 of the first cannula 2. According to alternate embodiments, an interlocking fit may be further accomplished by way of a snap fitting, a tongue and groove fitting, or other means of securing the first cannula 2 to the second cannula 12 that are known in the art. In an alternative embodiment, the cannula (2, 12) may be interlocked in a predetermined configuration that permits the cannula (2, 12) to 640 expand in telescoping fashion.

Figure 9:
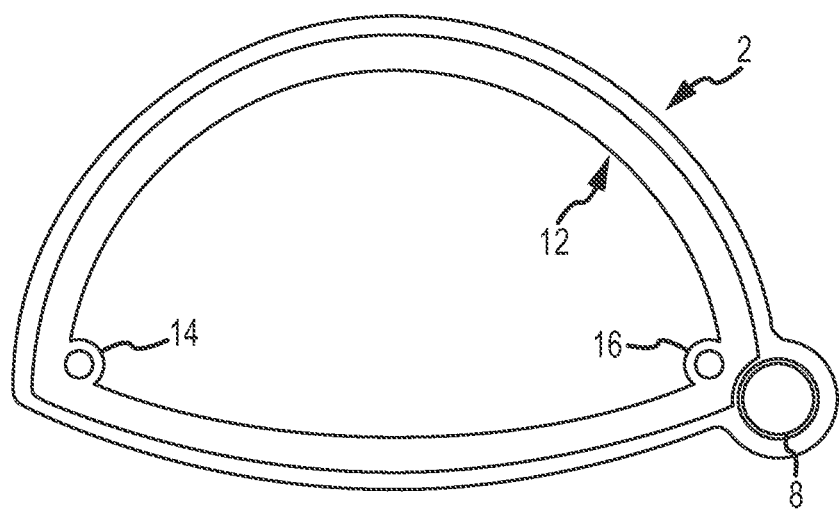
FIG. 9 is a cross-sectional view of the cannula shown in FIG. 8.

Referring now to FIG. 9, the first and second cannula 2, 12 are shown in a cross-sectional view. This assembly includes at least one channel or lumen 8 for inserting at least one fastening device, such as a screw, as well as two smaller lumens or channels 14, 16 which may be used for inserting one or more fiber optic strands/bundles for providing 645 enhanced illumination. These channels 14, 16 may run substantially the entire length of the second cannula 12, and may be greater or fewer in number than shown in FIG. 9. The objective of providing these channels 14, 16 on the interior of the cannula assembly is to provide sufficient lighting to allow the surgeon to view the surgical site and complete the surgery without visual impairment.

Figure 10:
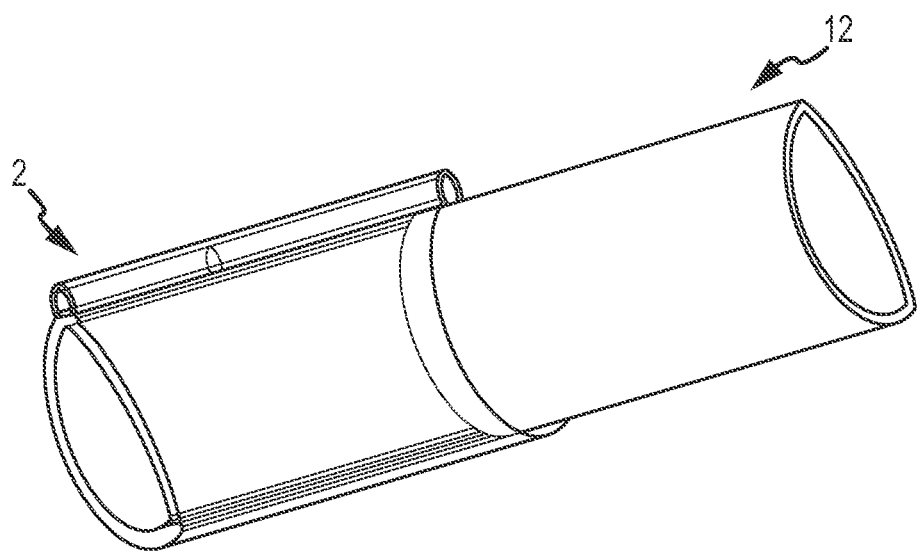
FIG. 10 is a view of the cannula of FIG. 9 in a docked view.

Referring now in detail to FIG. 10, the first and second cannula 2, 12 are shown in a docked or assembled state. The second cannula 12 may vary in length to accommodate surgery taking place in various portions of the patient's body, and according to alternate embodiments may be asymmetrical about its length, thereby providing a larger opening at one end than the distal end which mates with the first cannula 2. Thus, in operation, the first cannula 2 is secured by way of a fastening member such as a screw, and then the second cannula 12 is inserted into the first cannula 2. According to a preferred embodiment, one or more of the cannula 2, 12 shown in FIG. 10 may be disposable. According to alternate embodiments, the cannula 2, 12 shown in FIG. 10 may be reusable.

Figure 11:
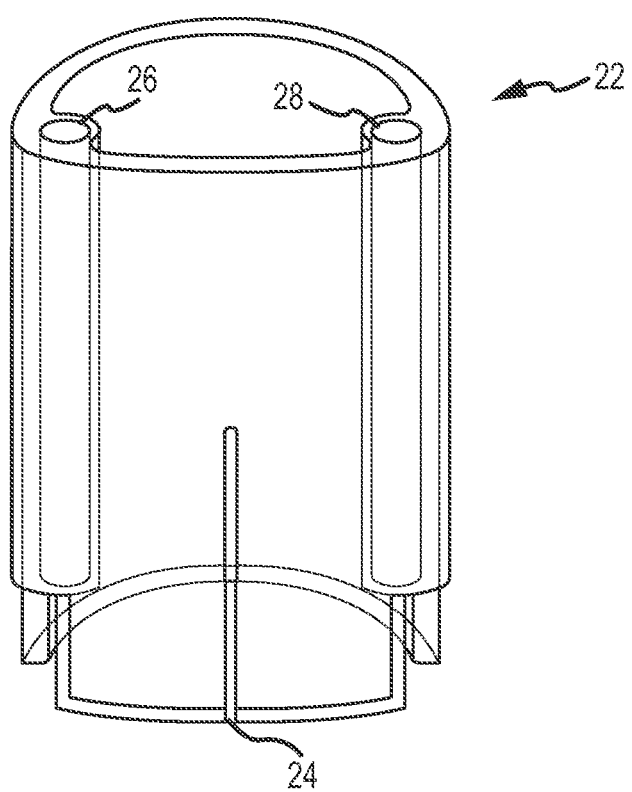
FIG. 11 is a perspective view of a cannula with at least one channel for inserting an anchoring device and at least one slot for mating with an illumination and/or video insert according to one embodiment of the present disclosure.

FIG. 11 shows a perspective view of a cannula 22 with at least one slot 24 for accommodating compression or expansion of the tubular body of the cannula 22. Similar to the second cannula 12 discussed above, this cannula may be inserted into the base cannula 2 which is secured to the surgical site. This cannula 22 also includes channels 26, 28 for inserting one or more fiberoptic bundles for providing illumination.

Figure 12:
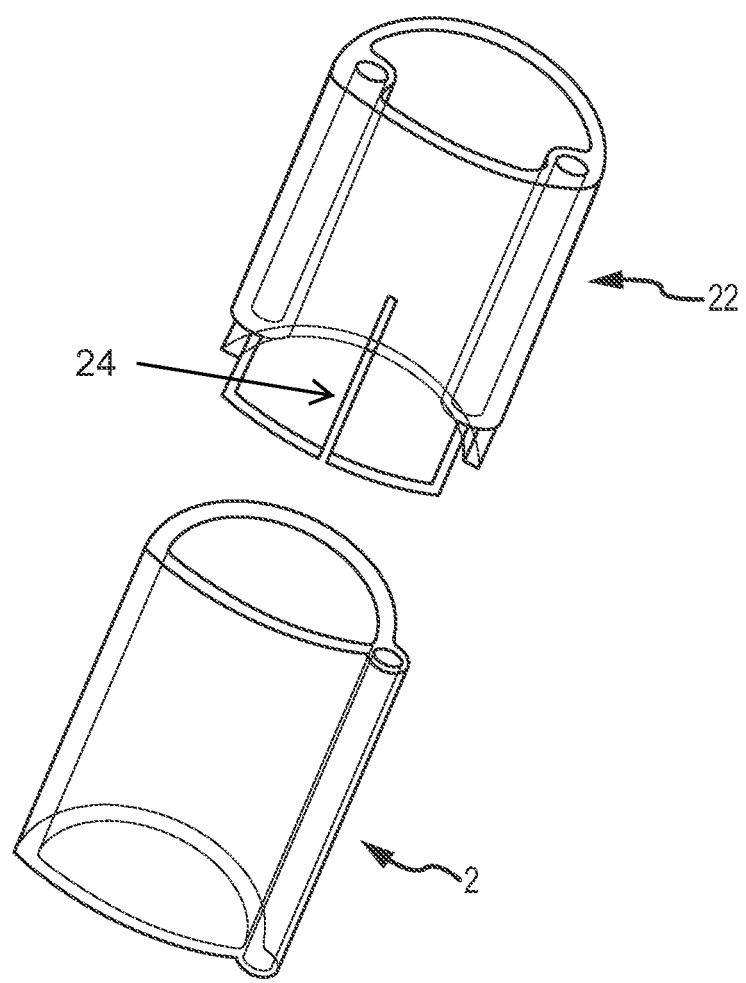
FIG. 12 is a perspective view of the cannula of FIG. 11 and the cannula of FIG. 7.
Figure 13:
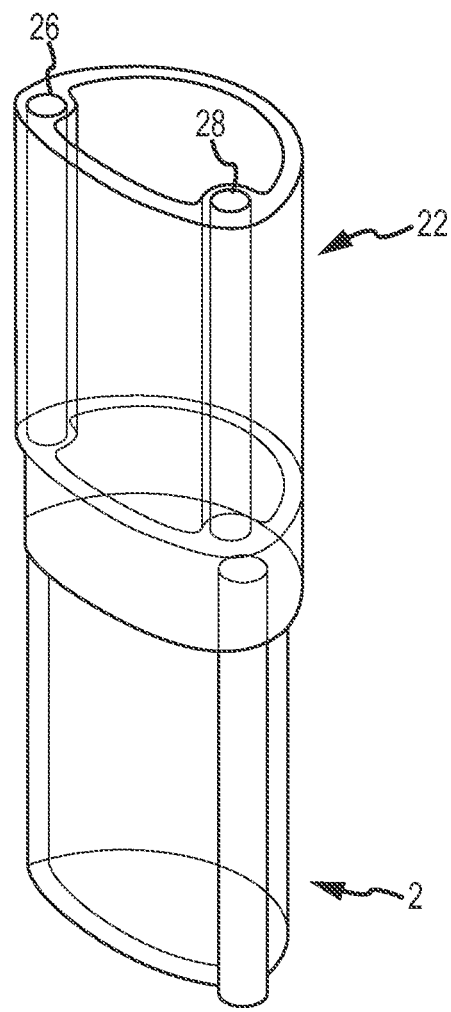
FIG. 13 is a perspective view of the cannula of FIG. 12 in a docked view.

Referring now to FIG. 12, the cannula 22 of FIG. 11 is shown with the cannula 2 of FIG. 7, and is oriented in a manner to permit interlocking between the first cannula 2 and this slotted cannula 22. FIG. 13 shows the cannula 22 of FIG. 11 and the cannula 2 of FIG. 7 in a docked or assembled position. This docking occurs similar to that described in relation to FIG. 8 above, such that there is a compression fit between the two cannula 2, 22, although in FIG. 13 cannula 22 is depicted fitting over cannula 2. In certain embodiments, the placement of the slotted cannula 22 on the base cannula 2 does not interfere with the surgeon's ability to remove or replace the fastening member. This assembly therefore provides an extended cannula which includes channels 26, 28 for inserting one ore more fiberoptic bundles to provide adequate lighting. These channels 26, 28 may also provide a location for securing an insert which may provide video capabilities within the tubular body of the cannula assembly, either hardwired or wirelessly. In another embodiment, multiple slotted cannula, similar to cannula 22, may be joined such that the slot(s) in a first slotted cannula aligns with the slot(s) in a second slotted cannula.

Figure 16:
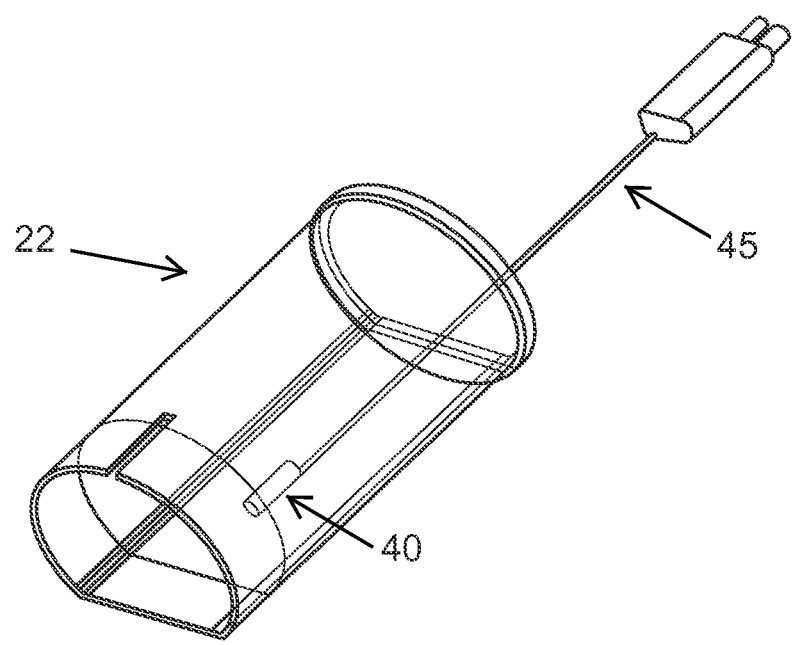
FIG. 16 is a perspective view of the cannula according to one embodiment with a hardwired CMOS/CCD camera device insert.

Referring now in detail to FIG. 16, a camera insert 40 which may be inserted into a slot of the cannula 22. Accordingly, the base cannula 2 which has been secured to the operating site is then coupled to the slotted cannula 22. Once the slotted cannula 22 is in place, a tool 45 may be used to insert the camera insert 40 into the cannula 22 as shown in FIG. 16. Subsequently, the tool 45 may be removed, or alternatively the tool 45 may incorporate electrical leads to the insert and remain in the slot of the cannula 22 during the surgery. Additional illumination, including by one or more fiber optic strands/bundles (not shown in FIG. 16) may also be provided to accommodate lighting insert. According to one embodiment, the camera insert 40 provides both video capabilities and illumination to the surgical site. Further description of the various camera technologies which may be incorporated in this design shown in FIG. 16 are described in detail herein, but expressly include CCD and CMOS technology.

According to an alternative embodiment, one or more light fibers/bundles may be fashioned in an annulus around the camera insert 40 to provide illumination to the surgical site. In still another embodiment, the light fibers may be replaced by LEDs in a remote light source or at the distal-tip of the cannula 12 or the camera insert 40. The light source may come from an external device such as a headlight lamp, or a standard-type light source commonly found in operating rooms which plugs into an adaptor on the cannula 12.

According to a preferred embodiment, the cannula described herein comprise at least one slot through which one or more camera device(s) can be inserted on a complimentary thin plastic composite stem-shaped insert, which preferably fits in a tongue and groove fashion along the tubular body of the cannula. The camera device(s) with associated wide-angle optics and its composite holder can be removed during the course of the operation for cleaning or when the cannula needs to be re-directed during the course of the surgery. The camera device, which according to a preferred embodiment is based on either CCD or CMOS technology, may have the necessary video-processing circuitry onboard the camera chip housing or the video-processing circuitry may be housed several meters away from the camera chip and connected by a cable or via wireless transmission.

Figure 14:
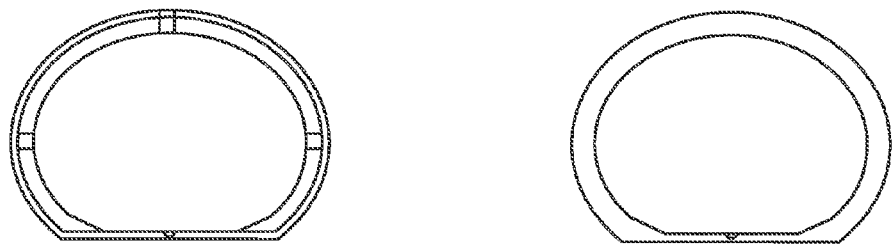
FIG. 14 includes a cross-sectional view of the cannula, according to one alternative embodiment, with LED illumination devices and a CMOS/CCD camera slot, and a top plan view of the cannula according to this embodiment.

Referring again the drawing figures, FIG. 14 shows two views of a cannula which incorporates light emitting diode or "LED" illumination devices and at least one slot for incorporating a CMOS or CCD camera insert into the cannula wall. As shown in FIG. 14, the cannula is generally ovoid in shape (as viewed in cross-section or in a top plan view), and has at least one inwardly facing shoulder, through which one or more LED's may be inserted or secured for providing illumination about the interior of the cannula. According to a preferred embodiment, the cannula further comprises at least one planar wall, which breaks the generally ovoid shape of the cannula, and it is about this planar surface that the CMOS or CCD camera insert is preferably secured.

According to a preferred embodiment, the CMOS or CCD camera insert is inserted into a slot or groove or channel which is formed about one interior wall of the planar surface of cannula as shown in FIG. 14. Alternatively, the CMOS or CCD camera insert can be attached by other means, such as by using fastening devices known in the art, or by attaching magnetically, for example, by way of one or more neodymium magnets.

According to the embodiment shown in FIG. 14, the inwardly facing shoulder creates an interior plane (as viewed in cross-section) which accommodates the coupling of a progressive cannula, thereby extending the overall length of the cannula. Thus, one or more of the progressive cannula, which may be coupled together in a telescoping arrangement, may be disposable, reusable, etc.

Figure 15:
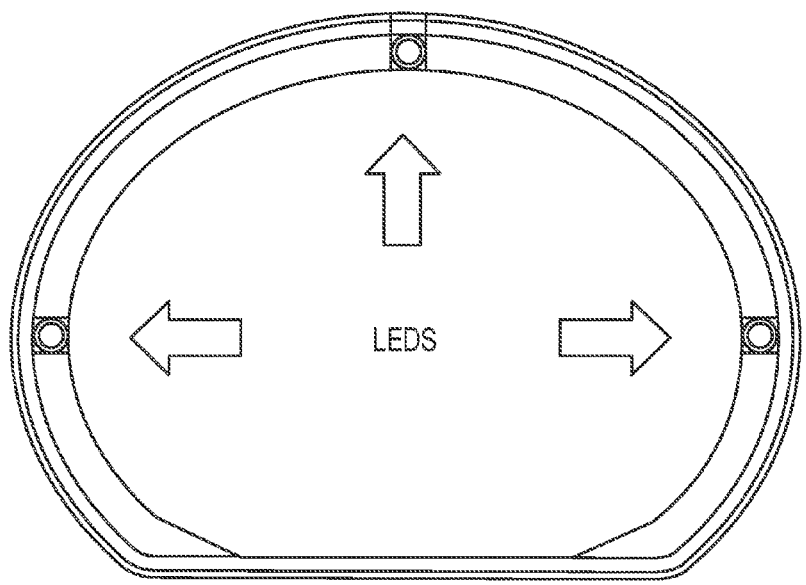
FIG. 15 is a detailed cross-sectional view of the cannula shown in FIG. 14.

FIG. 15 shows a more detailed view of the location of the LED devices, which according to a preferred embodiment are at least three in number. The LED devices are preferably spaced equidistance from one another and at opposite poles of the generally ovoid cross-sectional shape of the cannula. According to alternate embodiments, fewer or greater number of LEDs may be provided for providing sufficient illumination within the cannula, and it is expressly understood that locations other than those shown in FIGS. 14-15 are understood to be compatible with the nature of the invention disclosed herein.

Referring again to FIG. 16, a CMOS or CCD camera insert, which may be hardwired to a connector, is shown in a perspective view in relation to a progressive cannula according to one embodiment. As shown in FIG. 16, the CMOS or CCD camera insert may be inserted along the interior portion of the generally planar surface of cannula, to a certain depth of the cannula, such that it is positioned to capture images at the distal end of cannula (i.e., the end of the cannula closest to the surgical site).

As shown in FIG. 16, the distal end of the cannula may also comprise a exterior slot for securing to an anchor or guide wire, which may be affixed to one or more anatomical features located at or adjacent the surgical site. Alternatively, this slot may also facilitate connection of this cannula to one or more progressive cannula, and according to one embodiment may serve as a guide for one or more surgical syringes, such as the type typically used for bone marrow extraction.

The connector shown in FIG. 16 may be hardwired to the CMOS or CCD camera device, and is of a nature to connect to one or more display means, such as an LCD or LED or other video display. Thus, images captured by the CMOS or CCD camera device are transmitted via the connector to the display for viewing either still or live video images captured during the surgery.

Figure 17:
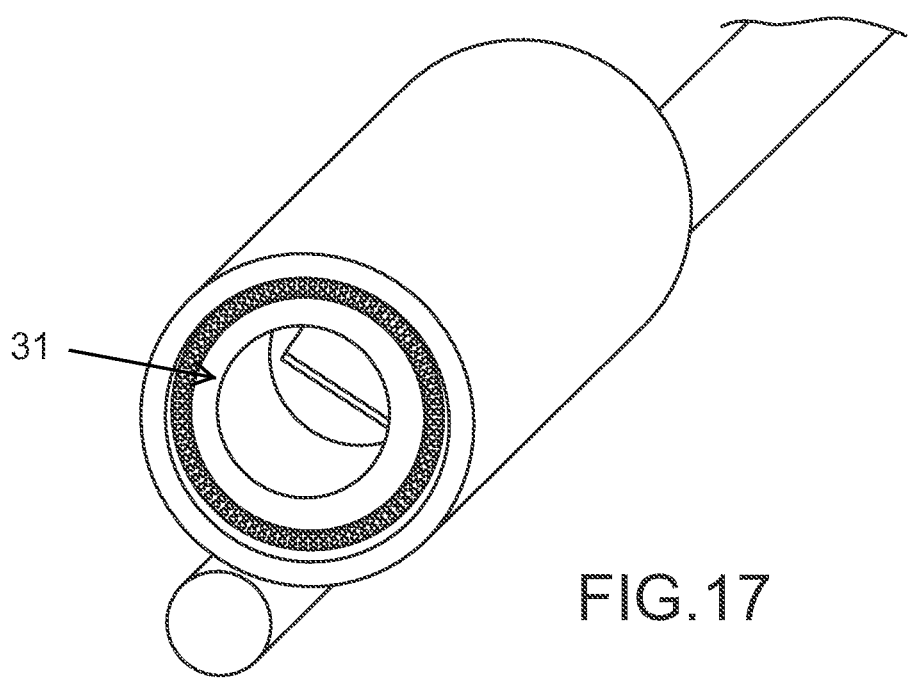
FIG. 17 is a detailed perspective view of the CMOS/CCD camera insert according to FIG. 16 with a fiber optic array.

Referring now to FIG. 17, a detailed perspective view of the CMOS or CCD camera device 31 and fiber optic array of illumination members are shown. According to this embodiment, the CMOS or CCD camera device 31 is protected by a housing, which is generally cylindrical and surrounds a portion of the CMOS or CCD camera device 31. At one end of the camera housing is an opening for the lens of the CMOS or CCD camera device 31, and also for the fiber optic array of illumination members. In this embodiment, the fiber optic array of illumination members substantially surrounds the lens of the CMOS or CCD camera device 31. These illumination members according to a preferred embodiment are fiber optic strands, which are arranged in one or more layers about the circumference of the lens of the CMOS or CCD camera device 31. The overall size of the CMOS or CCD camera device 31, fiber optic array of illumination members and camera housing are sufficiently small such that they do not interfere with the insertion of tools, implants, etc. in the body of the cannula and used by the surgeon during the surgical procedure. Other details regarding the CMOS or CCD camera insert are provided above in connection with FIGS. 7-13.

Figure 18:
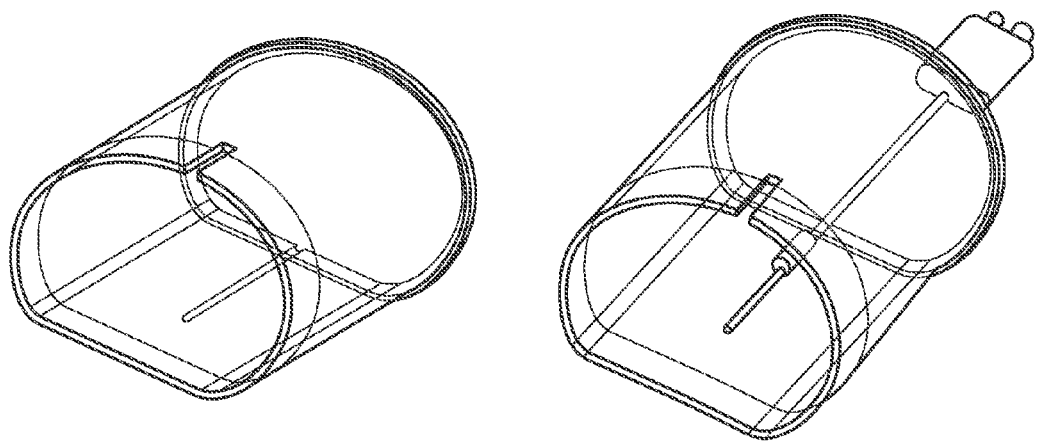
FIG. 18 includes perspective views of a cannula, according to another alternative embodiment, with and without the CMOS/CCD camera insert.

Additional views of the CMOS or CCD camera insert and the cannula according to a preferred embodiment are shown in FIG. 18. As shown in FIG. 18, the CMOS or CCD camera insert is attached to an insert which operates like a stem and slides longitudinally down one planar surface of the cannula where it engages a slot. This engagement between the insert and the slot secures the CMOS or CCD camera device to the interior of the cannula. The connector shown in FIG. 18 provides both power and the illumination necessary to operate the CMOS or CCD camera device, including the fiber optic array of illumination members.

Referring now to FIG. 19, a dilator assembly according to one alternate embodiment is shown. During a surgical procedure, it may be necessary for a initial probe, such as a slender dilator (also known as a pilot cannula) to be inserted into a small incision and used to probe the tissue between the incision and the surgical site. The pilot dilator may be used for this purpose, and may incorporate the video and/or illumination capabilities as described in more detail above. According to this alternative embodiment, the pilot dilator is approximately 2.5 millimeters to 10 millimeters in diameter.

Additional dilators/cannula may be inserted beside or over the first dilator in a progressive fashion until a sufficient pathway through the patient's tissue and anatomy has been formed for inserting one or more of the progressive cannula described above over these progressive dilators. By way of example but not limitation, a second dilator ranging in diameter from 7.5 millimeters to 12.5 millimeters may be placed over and around the first dilator, then a third dilator ranging in diameter from 10 millimeters to 15 millimeters may be placed over the second dilator, and a fourth dilator ranging in diameter from 12.5 millimeters may be placed over the third dilator. This step may be repeated several times by the surgeon, as necessary, until an adequate sized pathway is formed for inserting the cannula over the dilator assembly without causing trauma to the incision, the patient's anatomy, the surgical site, etc. It is expressly understood, although not depicted in FIG. 19, the video capabilities and illumination capabilities described herein may be incorporated with the pilot cannula and each of the first, second, third and fourth dilators described above (and any additional progressive dilators) for facilitating insertion, placement, and for achieving the other benefits described in the present disclosure.

Various figures (shown or incorporated by reference herein), e.g. FIGS. 20A-E, show the cannula 64 having an elliptical cross-section. In one embodiment, the ellipse has a width of about 20 millimeters in its major axis, and a width of about 16 millimeters in its minor axis. It will be appreciated that the cannula cross-section may be of a different size and have a different shape including, for example, an oval, a rectangle, a square, a rhombus, a trapezoid, a parallelogram, a polygon and a generally oblong shape such as an egg or football shape. As will be appreciated by one having skill in the art, the cross-sectional shape of the cannula 60 permits the user to employ instruments in the cannula that require movement or manipulation in one direction, preferably along the major axis, but to a lesser extent in the other direction. The oblong shape of the cannula 60 would permit, for example, rasps and curettes to be manipulated and used in a joint in a minimally invasive fashion. Similarly, the tool 32 can be manipulated and used in a joint even with the head 36 at any angle relative to the shaft. One having skill in the art will appreciate that the dimensional requirements of the cannula 60 will vary based on the length of the cannula, and the items or tools being inserted therein.

Figure 20A:
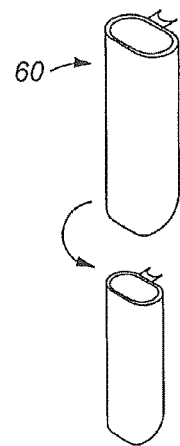
FIGS. 20A-20F are various views of a surgical cannula and dilators that are used in conjunction with certain embodiments of the present disclosure.
Figure 20B:
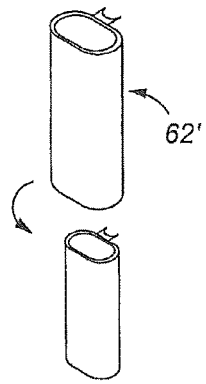
Figure 20C:
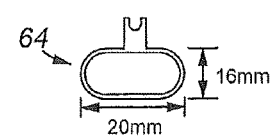
Figure 20D:
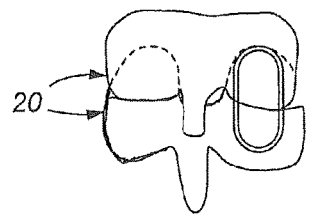

FIG. 20D shows two vertebrae 20 and a view of the footprint made by a cannula 60 in one embodiment of the present disclosure. As will be appreciated, the cannula 60 provides access to adjacent facets of two adjacent vertebrae. The oval or elliptical shape of the cannula 60, however, allows the procedure to be performed in a minimally invasive fashion by reducing the incision required to gain access to the surgical site and the reducing the tissue exposed during the procedure. FIG. 20E is a side aspect view of the cannula 60 placed over two adjacent vertebrae 20 separated by a joint space. The view in FIG. 20E is the side aspect view of the cannula 60 in, for example, FIG. 20D. FIG. 20E exemplifies another advantage provided by certain embodiments of the cannula 60 in the present disclosure in that it provides optimal access to a surgical site that may have anatomy or bone features that make it desirable to have, for example, an angled and/or curved end to the cannula. One having skill in the art will further appreciate that an ideally shaped cannula 60 will allow the user to more safely and reliably access the surgical site and will reduce the risk of injury to the surrounding tissue.

Figure 20F:
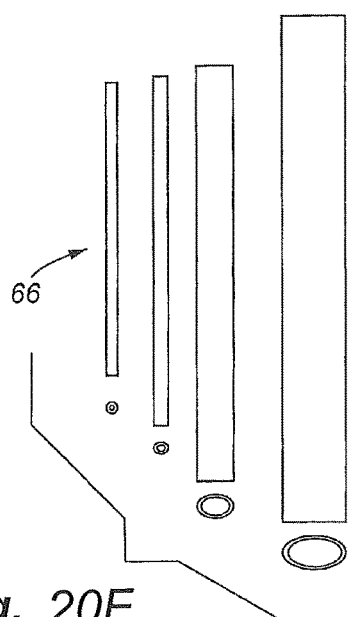
Figure 20E:
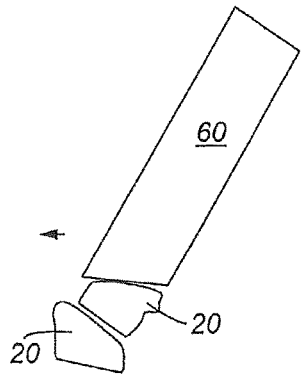

FIG. 20F shows the shaft and cross-sectional or end views of various dilators 66. The various dilators 66 shown are of various sizes, having various lengths and cross-sectional areas. As can be seen by the cross-sectional or end view of the dilators 66, the dilators 66, like the cannulae described above have an oval or elliptical shape. According to a preferred embodiment, one or more dilators may be used to dilate the muscle or other tissue of the patient to access the surgical site. A first slender dilator 66 is used to probe through the muscle or other tissue and to locate the desired vertebrae. Once that first slender dilator 66 is seated, additional dilators 66 may be inserted around the previously seated dilator 66 until the desired circumference through the muscle or other tissue is achieved. In this fashion, the first slender dilator 66 serves as a radiographic marker, and establishes the path for subsequent dilators 66 of greater circumference than the first slender dilator 66. This serves to reduce ischemic injury to the patient and reduces the time necessary to locate and access the desired vertebrae. The first slender dilator 66 has a sufficient circumference to be easily viewed by x-ray or other imaging technology when seating the dilator 66 on the desired vertebrae. The dilators 66 are variable in length, preferably ranging from 3-14 cm.

Once the dilators 66 have been used to dilate the muscle tissue surrounding the path to the desired vertebrae, a cannula 60 may be inserted into the interior circumference of the dilators 66. The cannula 60 according to a preferred embodiment is ovoid in shape to permit dissection from caudad to cephalad (as opposed to from medial to lateral) and further accommodate dissection about the facet joint. As with the dilators 66, the cannula 60 may be variable in length, ranging preferably from 3-10 cm, to accommodate varying depths from skin to bone. As mentioned above, the cross-sectional geometry of the cannula is preferably ovoid in shape, and in a preferred embodiment the major diametrical axis of the cannula is about 20 mm, and the minor diametrical axis of the cannula is about 16 mm.

Varying embodiments of the cannula described herein may further comprise an angled or sloped surface at one distal end of the cannula for accommodating access and viewing of an implant site that is not directly below the incision. By way of example but not limitation, a surgeon may use one or more of the angled cannula shown in FIGS. 20A-20F in conjunction with the dilators 66 described herein to probe through the muscle or other tissue using an angled approach, thereby allowing access to a specific vertebrae either above or below the vertebrae directly below the incision. Once the dilators have been used to clear a path through the muscle or other tissue at an angled approach, the angled cannula may be inserted with the angled or sloped surface oriented so that the angled or sloped surface rests near horizontally against the vertebrae, as shown in the appended Figures. This angled cannula assists the access and visibility of additional vertebrae without requiring additional incisions, and further permits securing fastening devices such as screws using an angled approach. As with the other cannula described above, the cross-sectional shape of the angled cannula is preferably ovoid in shape, and the entire longitudinal length of the angled cannula may be slightly greater than the other cannula described herein.

According to one particular embodiment of the present disclosure, a system is provided where the cannula/dilator tools further include one or more electrical probes 51 at the exit portal, which are adapted to assist the surgeon in identifying the presence and location of nerves as the probe is advanced during minimally-invasive surgery, thereby providing a device for guiding the path of other surgical instruments to be inserted into the intervertebral space. For example, an expandable tip cannula 50 may be provided, which functions both as an access portal for spinal surgery and as a system for nerve surveillance, such that the presence and relative position of the nerves of the lumbo-sacral plexus can be detected as the expandable tip cannula 50 is inserted through the patient's fascia and musculature. One particular advantage of determining the position of the nerves with respect to the distal tip of the cannula is that the nerves can be avoided or gently moved out of the surgeon's way while inserting the cannula. This concept may also be incorporated in the one or more slender dilator tools described in detail herein.

According to another embodiment, the present disclosure provides a system of cannulas/dilators adapted to assist the surgeon in guiding the path of surgical instruments received into the intervertebral space, while identifying the presence and location of para-spinal nerves as the cannula/dilator is advanced to a patient's intervertebral space during minimally invasive surgery. In various aspects of the present disclosure, the probes may be comprised of one or more electrodes powered at a low level to sense the position of the nerves of the lumbo-sacral plexus through continuous real time electromyographic monitoring. Alternatively, these electrodes can be powered at a higher level such that they operate to cauterize blood vessels. Safety systems ensure that power levels sufficient to cause cauterization are not activated if a nerve is sensed to be near the electrodes at the distal end of the cannula/dilator.

The system according to one embodiment of the present disclosure includes providing illumination and video capability with a cannula having a shape other than round (e.g., oval, pointed, square cornered, etc.) and having an end (e.g., the end inserted into the patient, distal from the user) that is angled and/or shaped to be ideally seated in a surgical site. Asymmetrical cannulas may allow visualization of the facet joint, and an "egg-shaped" cross section may allow for the best view of the facet joint and minimizes the medial-lateral dissection that a round cannula would require.

Still other aspects of the invention are directed to cannula instruments that have a patient contacting end that is adjustable to assume a predetermined conformation. Thus, in one embodiment, material forms the tip end that comes into contact with bone, tissue, and especially as it nears nerve tissue, with such cannula end material being malleable to an extent necessary for the surgeon to mold the end conformation such that it achieves desired avoidance of particular structures encountered in any particular surgery. Thus, if a bony outcropping, a nerve fiber, etc. is perceived by the surgeon, the cannula tip end can be adjusted to avoid undesired contact or interference with such tissues or structures. In particular embodiments, the ability to adjust the geometric parameters of the tip end is achieved by manipulation of the other end of the instrument. For example, providing a turnable component at the opposite end of the instrument, the shape of the other end of the instrument (i.e. the end inserted into the patient) can be adjusted to expand circumference, reduce circumference, render the opening more or less oblong, etc. In such a manner, it is possible to avoid having to remove the instrument or cannula from the patient's site to adjust the morphology of the instrument or cannula operating end, thus saving time, avoiding undesired reinsertion procedures, etc.

Certain embodiments of the surgical cannula, which may be used in conjunction with certain aspects of the present disclosure, include cannula having a bottom opening that is angled oblique to the top opening. These cannuale may be in correspondingly larger or smaller form factors so that they may become nested within one another for facilitating insertion in the patient. The cannula may have an elliptical cross-section. In one embodiment, the ellipse has a width of about 20 millimeters in its major axis, and a width of about 16 millimeters in its minor axis. It will be appreciated that the cannula cross-section may be of a different size and have a different shape including, for example, an oval, a rectangle, a square, a rhombus, a trapezoid, a parallelogram, a polygon and a generally oblong shape such as an egg or football shape. As will be appreciated by one having skill in the art, the cross-sectional shape of the cannula permits the user to employ instruments in the cannula that require movement or manipulation in one direction, preferably along the major axis, but to a lesser extent in the other direction. The oblong shape of the cannula would permit, for example, rasps and curettes to be manipulated and used in a joint in a minimally invasive fashion. Similarly, other tools can be manipulated and used in a joint at any angle relative to the shaft of the tool. One having skill in the art will appreciate that the specific dimensional requirements of the cannula will vary based on the length of the cannula, and the items or tools being inserted therein.

As will be appreciated, the cannula provides access to adjacent facets of two adjacent vertebrae. The oval or elliptical shape of the cannula, however, allows the procedure to be performed in a minimally invasive fashion by reducing the incision required to gain access to the surgical site and the reducing the tissue exposed during the procedure. Another advantage provided by certain embodiments of the cannula of the present disclosure is that it provides optimal access to a surgical site that may have anatomy or bone features that make it desirable to have, for example, an angled and/or curved end to the cannula. One having skill in the art will further appreciate that an ideally shaped cannula will allow the user to more safely and reliably access the surgical site and will reduce the risk of injury to the surrounding tissue.

Various dilators may be used (in connection with the cannula of the system described above) having various sizes, various lengths and cross-sectional areas. The dilators, like the cannula described above, may have an oval or elliptical shape. According to a preferred embodiment, one or more dilators may be used to dilate the muscle or other tissue of the patient to access the surgical site. According to a preferred embodiment, a first slender dilator is used to probe through the muscle or other tissue and to locate the desired vertebrae. Once that first slender dilator is seated, additional dilators may be inserted around the previously seated dilator until the desired circumference through the muscle or other tissue is achieved. In this fashion, the first slender dilator serves as a radiographic marker, and establishes the path for subsequent dilators of greater circumference than the first slender dilator. This serves to reduce ischemic injury to the patient and reduces the time necessary to locate and access the desired vertebrae. The first slender dilator has a sufficient circumference to be easily viewed by x-ray or other imaging technology when seating the dilator on the desired vertebrae. The dilators are variable in length, preferably ranging from 3-14 cm.

Once the dilators have been used to dilate the muscle tissue surrounding the path to the desired vertebrae, a cannula may be inserted into the interior circumference of the dilators. The cannula according to a preferred embodiment is ovoid in shape to permit dissection from caudad to cephalad (as opposed to from medial to lateral) and further accommodate dissection about the facet joint. As with the dilators, the cannula may be variable in length, ranging preferably from 3-10 cm, to accommodate varying depths from skin to bone. As mentioned above, the cross-sectional geometry of the cannula is preferably ovoid in shape, and in a preferred embodiment the major diametrical axis of the cannula is about 20 mm, and the minor diametrical axis of the cannula is about 16 mm.

Varying embodiments of the cannula described herein may further comprise an angled or sloped surface at one distal end of the cannula for accommodating access and viewing of an implant site that is not directly below the incision. By way of example but not limitation, a surgeon may use one or more of the cannula described herein in conjunction with the dilators described herein to probe through the muscle or other tissue using an angled approach, thereby allowing access to a specific vertebrae either above or below the vertebrae directly below the incision. Once the dilators have been used to clear a path through the muscle or other tissue at an angled approach, the angled cannula may be inserted with the angled or sloped surface oriented so that the angled or sloped surface rests near horizontally against the vertebrae. These cannula assist the access and visibility of additional vertebrae without requiring additional incisions, and further permits securing fastening devices such as screws using an angled approach.

As with the other cannula described above, the cross-sectional shape of the angled cannula is preferably ovoid in shape, and the entire longitudinal length of the angled cannula may be slightly greater than the other cannula described herein. According to another embodiment of the present disclosure, a system is provided where the cannula further include one or more electrical probes at the exit portal, which are adapted to assist the surgeon in identifying the presence and location of nerves as the probe is advanced during minimally-invasive surgery, thereby providing a device for guiding the path of other surgical instruments to be inserted into the intervertebral space.

An expandable tip cannula may be provided, which functions both as an access portal for spinal surgery and as a system for nerve surveillance, such that the presence and relative position of para-spinal nerves can be detected as the expandable tip cannula is inserted through the patient's facia and musculature. An advantage of determining the position of the para-spinal nerve with respect to the distal tip of the cannula in particular is that the para-spinal nerve can be avoided or gently moved out of the surgeon's way while inserting the cannula.

Accordingly, the present disclosure provides a system of cannulas adapted to assist the surgeon in guiding the path of surgical instruments received into the intervertebral space, while identifying the presence and location of para-spinal nerves as the cannula is advanced to a patient's intervertebral space during minimally invasive surgery. In various aspects of the present disclosure, the probes may be comprised of one or more electrodes powered at a low level to sense the position of a para-spinal nerve through continuous real time electromyographic monitoring. Alternatively, these electrodes can be powered at a higher level such that they operate to cauterize blood vessels. Safety systems ensure that power levels sufficient to cause cauterization are not activated if a nerve is sensed to be near the electrodes at the distal end of the cannula.

The present disclosure is also directed to an angled tool for use in performing spinal surgery procedures that includes illumination and/or video capabilities. According to a preferred embodiment, the angled tool is comprised of a longitudinal shaft, and has a first or operating end and a second or working end. The shaft is preferably tubular and has a bore running through the length of the angular tool suitable for receiving an insert. The insert further comprises CMOS or CCD video imaging device(s), which permit a user to view images captured by the at least one CMOS or CCD imaging device. According to one embodiment the insert and CMOS/CCD video imaging device(s) are disposable. In another embodiment they are reusable. In yet another embodiment, the angled tool further comprises one or more illumination devices arranged in an annulus around the one or more CMOS or CCD video imaging devices to enhance illumination at the surgical site.

In use, by providing one or more CMOS or CCD video imaging devices (which according to one embodiment further comprise at least one wireless transmitter for transmitting data wirelessly to at least one display) and illumination surrounding the video imaging devices, the surgeon has the ability to view and illuminate the patient operating site and/or the interior of the surgical cannula with the angled tool, in addition to any illumination that is provided by the cannula.

According to yet another embodiment of the present disclosure, a tool (other than the angled tool described above) is provided that comprises at least one CMOS or CCD video imaging device, which permits a user to view images captured by the CMOS or CCD imaging device of the disc space or other surgical area to be operated on. For example, one or more specula, curettes, awls, blades, scrapers, or other surgical tools may incorporate the video insert described in greater detail below, for capturing and viewing images of the surgical site after dissection has occurred. This may be accomplished by providing a CMOS or CCD camera at the distal end of the one or more tools, and either wirelessly or hardwire transmitting the images captured by that CMOS or CCD camera to a display.

According to another embodiment of the present disclosure, a tool is provided that comprises at least one CMOS or CCD video imaging device, which permits a user to view images captured by the CMOS or CCD imaging device of the disc space or other surgical area to be operated on. For example, one or more disc debridement tools may incorporate the video insert described in greater detail below, for capturing and viewing images of the intervertebral disc space after and during dissection. This capacity allows for a more complete and safe disc space preparation. A more precise carpentry of the disc space allows for an increased potential for fusion and a reduction of vertebral endplate or soft tissue injury. This may be accomplished by providing a CMOS or CCD camera at the distal end of the one or debridement tools, and either wirelessly or hardwire transmitting the images captured by that CMOS or CCD camera to a display.

Accordingly, the methods disclosed herein provide a surgeon viewing the operative site, instead of through the oculars of the microscope, but rather with the ability to view the patient's anatomy by presenting the images of the surgical site on a video screen or other display in front of him (or her) and in front of any assistant(s), consulting surgeons, hospital staff, etc. Due to the camera chip device and associated optics being placed directly at or immediately adjacent the operative site, the image collected is free from the distortions and the "field-flattening" effect commonly associated with complex optical stacks commonly used in operating microscopes and endoscopes. These novel apparatus and surgical methods result in a significant increase in "depth-cues" and color-reproduction. The camera device technology (preferably CCD or CMOS) provides a three dimensional-type picture to the surgeon with all necessary illumination and without the extra costs of adding a second camera and expensive intra-ocular optical orientations. The costs of the microscope and its maintenance, plastic draping, sterility/contamination issues and surgeon fatigue are either eliminated or substantially reduced.

A variety of other apparatus and methods may be employed in conjunction with the various aspects described herein to achieve fusion without departing from the spirit of the invention, such as the following apparatus and methods hereby incorporated by reference in their entireties: U.S. Patent Publication Nos. 2010/0137690 to Miles, et al.; 2009/0299411 to Laskowitz, et al.; 2009/0299412 to Marino; 2009/0299477 to Clayton, et al.; 2009/0275995 to Truckai, et al.; 2009/0287262 to Bertagnoli; and U.S. Pat. No. 7,621,955 to Goble, et al. Accordingly, additional apparatus, such as a refractor or distractor may incorporate the use of fiberoptic bundles and/or camera inserts described in relation to FIGS. 6-8 above. In particular, according to one embodiment of the present disclosure, a retractor device may incorporate one or more camera inserts along the shaft of the retractor similar to the camera insert described in relation to FIG. 16 above. Also, one or more fiberoptic bundles may be integrated with the insert, or alternatively run along independent lumens or channels along the arms of the retractor or distractor device.

Figure 21:
FIG. 21 is a cross-sectional view of various features of the present invention.
Figure 21:
Figure 21:
Figure 21:
Figure 21:

FIG. 21 depicts cross-sectional views of various cannulas 10, 12, 15, 17, 18 and is further illustrative of how these aspects of the present invention interoperate. Although FIG. 21 depicts a single pilot cannula 10 and four dilator cannulas 12, 15, 17, 18, one of ordinary skill in the art will recognize that the present invention is not limited to any specific number or shape of cannula. It will further be recognized that cannulas of different cross-sections would also serve the spirit of the present invention, so long as that when cannulas of increasing size are inserted, these larger cannulas do not expand the surgical area uniformly in all radial directions. For example, cannulas of triangular, elliptical, ovoid, egg-shaped or other similar cross-sectional shapes may also achieve objects of the present invention. In various embodiments, features of the present invention comprise conical, bullet-shaped, or tapered distal ends so as to facilitate their insertion and expand tissue rather than cutting or tearing and thereby reducing injury to a patient.

These cannulas, which may be inserted in progressively larger sizes (as will be described later), are constructed or formed in this manner so as to avoid or mitigate complications presented with the prior art (as described above). Specifically, the insertion of these cannulas with asymmetric cross-sections allows a user to expand the surgical area without expanding into a specific region(s) where the device may impinge upon nerves and other tissue.

Additionally or in place of a guide pin, a pilot cannula of slightly larger diameter may be inserted. This pilot cannula may either be placed around or proximal to the guide pin. The pilot cannula may further include means, such as conductive wires and sensors, to detect the proximity of nerves and nerve structures. Guide pins and/or pilot cannula(s) may further be used to direct the location of various dilators which may gradually expand the desired surgical area in a non-concentric or radially non-uniform fashion so as to allow adequate room for surgical tools and procedures, with reduced risk of impinging upon nerves. Specifically, dilators of the present invention are shaped in an asymmetric fashion so as to expand the surgical area in a defined radial direction(s) and to avoid impingement of the areas with higher concentrations of nerve structures.

Various devices of the present invention include anchoring means, such as screws and/or tangs and stakes to secure the devices once located in a desired position. These anchoring means further operate to reduce the risk of injury to the patient as repositioning or re-insertion of these and similar devices further increase the risk of damaging surrounding nerves and tissue. Once a sufficient degree of dilation of a surgical area is achieved, smaller cannula disposed within the larger cannula may be removed to allow for visibility and usable space within devices of larger diameters. Devices of larger diameters, such as dilators of an appropriate size, retractors, and working cannulas may be employed to stabilize the surgical area. These devices, including an outer working cannula, may be secured by previously discussed anchoring means or by external mounting devices. Outer working cannula, as will be apparent from the present disclosure, may include various additional features such as fiber-optic lighting elements, imaging equipment, luminescent materials, bioluminescent materials, etc.

Figure 22:
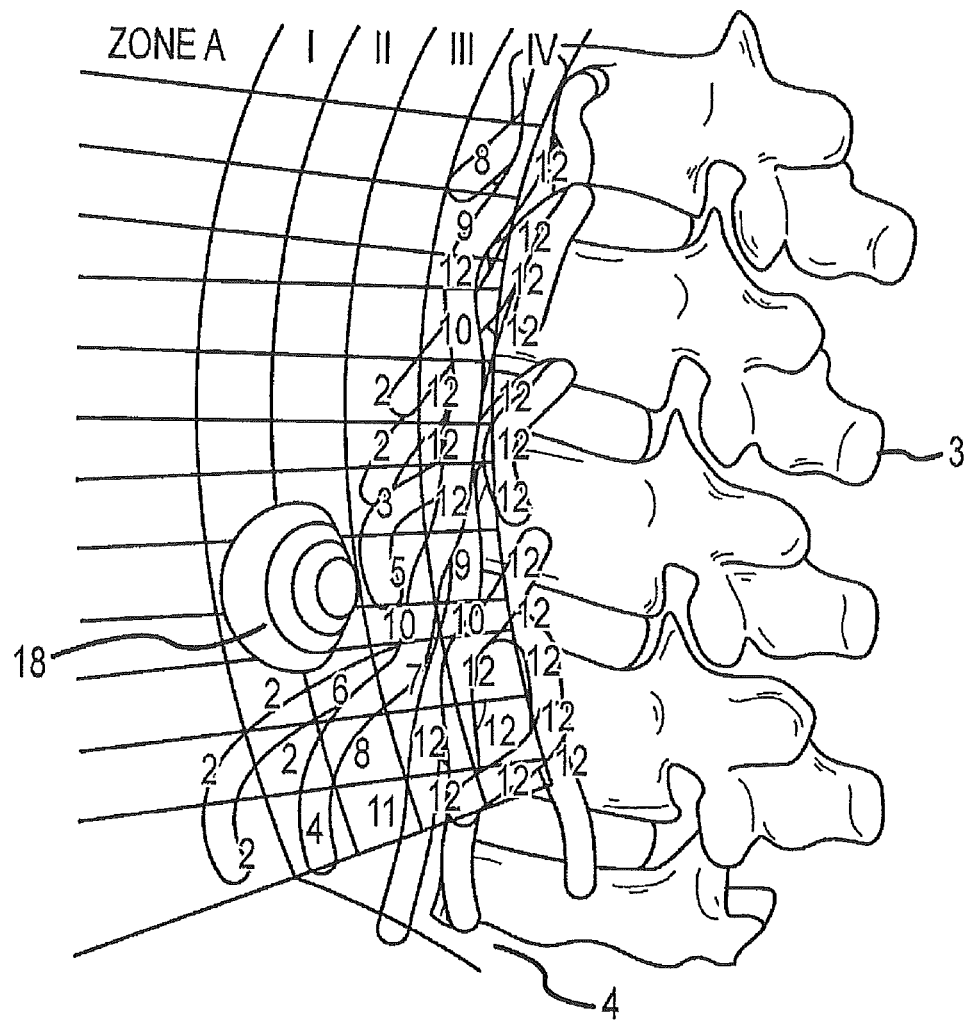
FIG. 22 is a cross-sectional illustration of a patient illustrating features and operation of the present invention.

FIG. 22 is a cross-sectional illustration of a patient wherein the non-working dilator cannulas have been removed from the cavity. FIG. 22 further illustrates a formed surgical cavity of sufficient size with minimal impingement upon the psoas and other nerves. Specifically, as consecutively larger devices are inserted, expansion is achieved in a direction away from areas III and IV as shown in FIG. 22. Expanding the work area in this manner provides for reduced risk of impinging upon nerves by avoiding areas of the greatest concentration of nerves.

Figure 23:
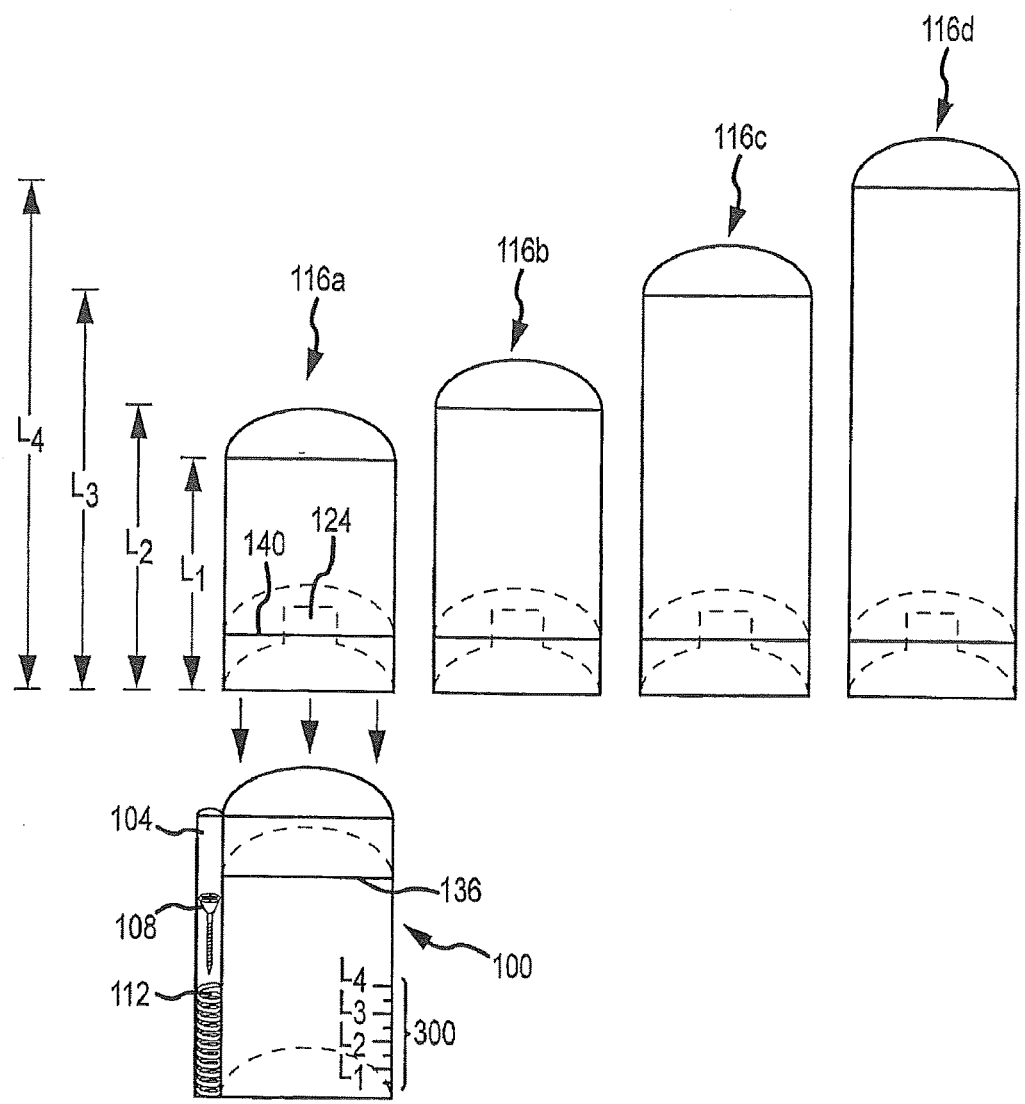
FIG. 23 is a perspective view of a cannula and working cannula according to one embodiment of the present invention.

FIG. 23 depicts a working cannula 100 and a plurality of extension cannulas, 116a, 116b, 116c, 116d, which may be fiber optic cannulas. In one embodiment, the working cannula 100 and a fiber optic cannula of the present invention comprise means for engaging one another and/or maintaining communication between the fiber optic cannula 116 and the working cannula 100. As further shown in FIG. 23, a plurality of fiber optic cannulas 116a, 116b, 116c, 116d may be provided, each having a different length ($L_1$, $L_2$, $L_3$, $L_4$). Different lengths are provided in order to provide for a final combined structure (i.e. 100 and 116 combined) with a proximal end disposed at an appropriate distance from a patient and skin edge. In one embodiment, indicia 300 are provided on a working cannula 100 which, when inserted into a surgical work area to the appropriate depth, reveal the corresponding fiber optic cannula which should be utilized.

Figure 24:
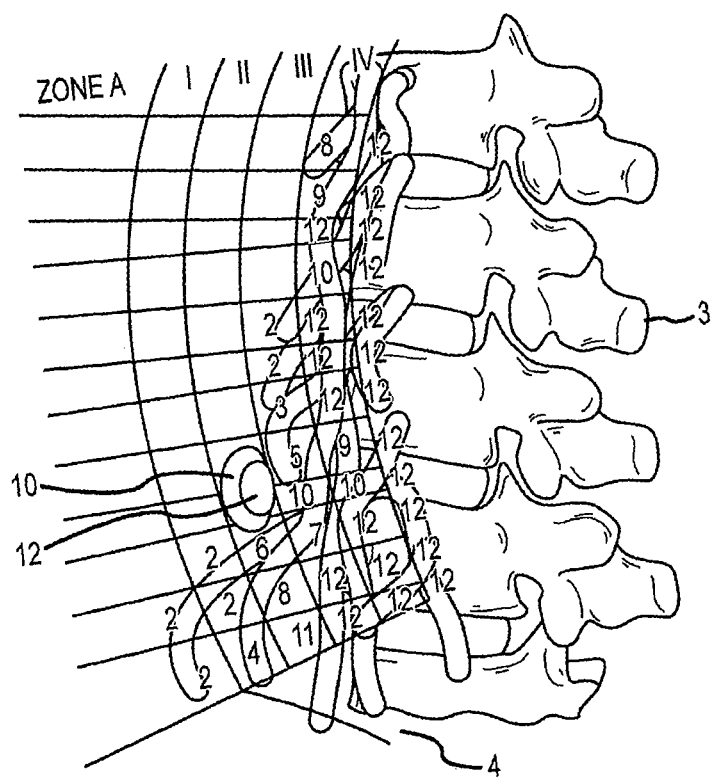
FIG. 24 is a cross-sectional illustration of a patient illustrating features and operation of the present invention.

FIG. 24 is a cross-sectional illustration of a patient illustrating features and operation of the present invention. FIG. 24 illustrates features of the previously discussed embodiments with reference to a patient's spine 3 and nerve structure 24. As one of ordinary skill in the art will recognize, the present invention allows for expansion and enlargement of the surgical area in a non-uniform manner. Accordingly, as shown in FIG. 24, enlargement of a surgical cavity may be achieved without impinging upon nerves or specific regions of a patient.

Figure 25:
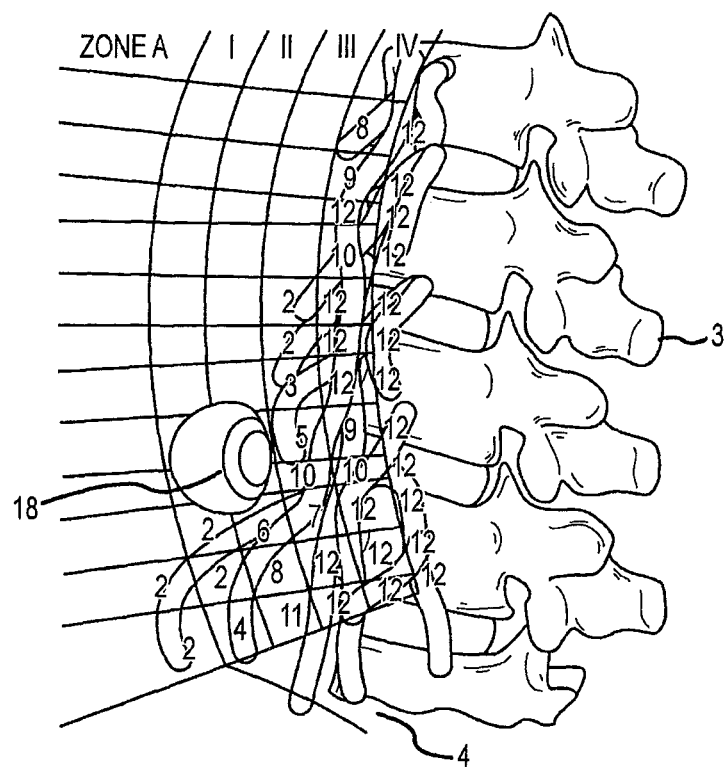
FIG. 25 is a cross-sectional illustration of a patient illustrating features and operation of the present invention.

FIG. 25 is another cross-sectional illustration of a patient illustrating features and operation of the present invention. FIG. 25 depicts multiple asymmetric cannulas in relation to a patient's spine 3 and nerve structure 4. Once the working cannula 18 (i.e. the cannula of largest desired diameter) is secured, remaining dilator cannulas are removed. In this manner, the psoas and other tissues are parsed so as to allow for access for spinal surgery and a working aperture is provided. It will be recognized that the working cannula need not be of any specific size or order to achieve the previously described sequence. Various factors, including patient size, procedure(s) to be performed, and/or tools to be used may determine the appropriate size of the working cannula.

For example, in one embodiment the working cannula 100 comprises a docking ridge 136 which comprises a generally annular protrusion from either a portion or the entirety of the outer circumference of the working cannula 100. The fiber optic cannula 116 may comprise a corresponding ridge or recession 140 at a variety of locations along its longitudinal length, which is adapted to receive the docking ridge 136 of the working cannula 100. In one embodiment, the outer diameter of the docking ridge of the working cannula is greater than both the outer diameter of the main portion of the working cannula and the inner diameter of the fiber optic cannula.

The fiber optic cannula is capable of expanding, for example, due to the inclusion of a compression gap 124. Thus, the fiber optic cannula may be elastically expanded around both the working cannula 100 and the docking ridge 136, and be slid or translated into a position where the docking ridge mates or corresponds with the receiving portion of the fiber optic cannula 116. In an alternative embodiment, docking between a fiber optic cannula 116 and a working cannula 100 is accomplished through one or more non-annular or non-rib like protrusions. For example, one or more protuberances of various sizes and shapes may be provided which interact and dock with corresponding features (e.g. female receiving portions) of a fiber optic cannula 116. One of skill in the art will recognize that receiving (or female) and corresponding (male) docking members may be disposed either on the working cannula 100 and/or the fiber optic cannulas 116a, 116b, 116c, 116d and the present invention is not limited to an embodiment wherein male or female docking portions reside on only one of the contemplated devices. Indeed, male and female portions may reside on either the working, fiber optic, or both cannulas.

In one embodiment, the compression gap of the fiber optic cannula 116 relies on the elastic abilities of the fiber optic cannula.116 to expand, accommodate a working cannula 100, and retract to (or approximately to) an initial position. In alternative embodiments, fiber optic cannulas 116 of the present invention comprise a compression gap 124 and/or additional devices useful for and capable of restricting an outer dimension of the fiber optic cannula 116 and thereby securing or attaching the fiber optic cannula 116 to a working cannula 100 or similar device. For example, various known devices may be employed to restrict an outer dimension of the fiber optic cannula, including but not limited to various straps comprising buckles, Velcro, teeth and receiving portions and adjustable strap fasteners.

As shown, working cannulas 100 are provided with at least one cylindrical housing 104 disposed on an exterior portion of the working cannula 100. As will be recognized, and as is described herein, working cannulas are not limited to any particular asymmetric geometry. Thus, D-shaped cross sections, U-shaped cross sections, and a variety of other combinations and alternatives, including crescent-shaped cross-sections, to the cross-sectional shapes are contemplated for use with working cannulas of the present invention.

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g. the use of disposable components comprising some or all of the apparatus described herein, as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A cannula system for accessing a surgical target site, comprising:
    a plurality of sequentially sized dilator cannulas deliverable along a path to a targeted surgery site to create an operative corridor;
    the plurality of sequentially sized dilator cannulas having a first end, a second end, and a longitudinal length therebetween, at least one of said sequentially sized dilator cannulas having a first end and a second end and a generally tubular body therebetween, said plurality of dilator cannulas having a non-circular cross-sectional shape having multiple radii of curvature the cross-sectional shape being symmetric about a first plane and asymmetric about a second plane, the first plane and second plane being disposed substantially perpendicular to one another, and wherein the cross-sectional shape comprises an inwardly deflecting portion such that a perimeter of the cross-section comprises at least two points of inflection;
    a pilot member being configured to introduce said plurality of dilator cannulas toward the targeted surgery site to create an operative corridor to said surgical target site, said pilot member passing through a bore in said at least one of said sequentially sized dilator cannulas, said bore formed through the generally tubular body and extending from the first end to the second end;
    wherein one of said sequentially sized cannulas is a working cannula that maintains the operative corridor, said working cannula having an inner surface defining a path for receiving surgical instruments, and wherein the dilator cannulas progressively expand the operative corridor so as to avoid impingement of areas with higher concentrations of nerve structures.

2. The cannula system of claim 1, wherein the cannulas are coupled to one another by way of a compression fit.

3. The cannula system of claim 1, wherein the working cannula has an oblong, elliptical cross-section with a width of about 20 mm about a major axis and a width of about 16 mm about a minor axis, said working cannula being from 3 cm to 10 cm in length.

4. The cannula system of claim 1, wherein the working cannula has a shape selected from the group consisting of crescent-shaped, half-sphere shape, half-oval shape, and half round cross-sectional shape.

5. The cannula system as set forth in claim 1, wherein the cannulas are secured to each other by an interlocking fit that permits the cannula system to expand in a telescoping fashion.

6. The cannula system as set forth in claim 1, further comprising a camera insert comprising one or more CMOS or CCD camera devices.

7. The cannula system as set forth in claim 6, wherein said one or more CMOS or CCD devices have at least one wireless transmitter for transmitting images captured by the one or more CMOS or CCD devices to a display.

8. The cannula system of claim 1, wherein said sequentially sized cannulas have a shape that is asymmetrical to allow visualization of a facet joint.

9. The cannula system as set forth in claim 1, wherein the cannulas are disposable and interlocked in a predetermined configuration that permits the cannula system to expand in a telescoping fashion.

10. The cannula system as set forth in claim 1, further comprising a camera insert comprising one or more CMOS or CCD camera devices; at least one slot disposed on an interior surface of the bore of the cannula configured to receive the camera insert within the at least one slot of the cannula; and at least one second channel configured to insert one or more illumination devices.

11. The cannula system as set forth in claim 10, wherein said one or more CMOS or CCD devices have at least one wireless transmitter for transmitting images captured by the one or more CMOS or CCD devices to a display.

12. The cannula system according to claim 1, wherein one or more illumination devices are operably associated with said working cannula, said illumination devices comprised of fiber optic strands or bundles.

13. The cannula system according to claim 1 wherein one or more illumination devices are arranged circumferentially along at least one of said cannulas.

14. The cannula system according to claim 1, wherein the shape of the cannulas have an egg-shaped cross section.

15. The cannula system according to claim 1, further comprising a probe comprised of one or more electrodes powered at a low level to sense the position of nerves.

16. The cannula system according to claim 1, wherein at least one of the cannulas is an expandable tip cannula which functions both as an access portion for spinal surgery and as a system for nerve surveillance, such that the presence and relative position of para-spinal nerves of a patient can be detected as the expandable tip cannula is inserted through the patient's facia and musculature.

17. The cannula system according to claim 1, wherein said cannulas are asymmetrical about their lengths.

18. The cannula system according to claim 1, wherein the surgical target site is the facet joint of a patient and said cannulas allow visualization of the facet joint of the spine.

19. The cannula system according to claim 1, wherein said cannulas are disposable.

20. The cannula system according to claim 1, wherein said cannulas include channels for inserting one or more fiber optic bundles for providing illumination.

21. The cannula system according to claim 1, wherein at least one of the plurality of sequentially sized dilator cannulas has an angle at the second end.

22. The cannula system according to claim 1, wherein said second end of said cannulas has a curved distal end.

23. The cannula system according to claim 1, wherein said cannulas have sloped surfaces at their second end for accommodating access in viewing of an implant site.

24. The cannula system according to claim 1, wherein said cannulas have bottom openings and top openings, said bottom openings being angled oblique to the top openings.

25. The cannula system according to claim 1, further comprising a screw for securing the cannula system to the surgical target site.

26. The cannula system according to claim 1, wherein at least one of the cannulas include at least one channel for inserting a screw.

27. The cannula system according to claim 1, wherein the cannulas are interlocking cannulas.

28. The cannula system according to claim 1, wherein said cannulas are configured to be interlocked in a predetermined configuration that permits said cannulas to expand in a telescoping fashion.

29. The cannula system according to claim 1, wherein at least one of the cannulas has a wall thickness that is uniform and does not vary in thickness around the perimeter of the cannulas.

* * * * *